United States Patent
Xu et al.

(10) Patent No.: US 10,814,302 B2
(45) Date of Patent: Oct. 27, 2020

(54) PRODUCING C5 OLEFINS FROM STEAM CRACKER C5 FEEDS—A PROCESS USING A CATALYTIC DISTILLATION REACTOR SYSTEM

(71) Applicant: LUMMUS TECHNOLOGY LLC, Bloomfield, NJ (US)

(72) Inventors: Yongqiang Xu, Pasadena, TX (US); Peter Loezos, Houston, TX (US); Willibrord A. Groten, Pasadena, TX (US); Romain Lemoine, Houston, TX (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 0 days.

(21) Appl. No.: 16/707,197

(22) Filed: Dec. 9, 2019

(65) Prior Publication Data

US 2020/0108368 A1    Apr. 9, 2020

Related U.S. Application Data

(62) Division of application No. 16/379,414, filed on Apr. 9, 2019, now Pat. No. 10,543,475, which is a division
(Continued)

(51) Int. Cl.
*B01J 19/24*     (2006.01)
*C07C 6/04*      (2006.01)
(Continued)

(52) U.S. Cl.
CPC .......... *B01J 19/242* (2013.01); *B01J 8/001* (2013.01); *B01J 8/0453* (2013.01); *C07C 5/03* (2013.01);
(Continued)

(58) Field of Classification Search
USPC ....... 585/324, 329, 330, 258, 259, 261, 360, 585/362
See application file for complete search history.

(56) References Cited

U.S. PATENT DOCUMENTS

| 5,464,504 A | 11/1995 | Beauford |
| 5,595,634 A * | 1/1997 | Hearn ................. B01D 3/009 203/29 |

(Continued)

FOREIGN PATENT DOCUMENTS

CN    1412165 A    4/2003

OTHER PUBLICATIONS

Office Action issued in related U.S. Appl. No. 15/901,415, dated Jan. 7, 2020 (31 pages).
(Continued)

*Primary Examiner* — Thuan D Dang
(74) *Attorney, Agent, or Firm* — Osha Liang LLP

(57) ABSTRACT

Producing C5 olefins from steam cracker C5 feeds may include reacting a mixed hydrocarbon stream comprising cyclopentadiene, C5 olefins, and C6+ hydrocarbons in a dimerization reactor where cyclopentadiene is dimerized to dicyclopentadiene. The dimerization reactor effluent may be separated into a fraction comprising the C6+ hydrocarbons and dicyclopentadiene and a second fraction comprising C5 olefins and C5 dienes. The second fraction, a saturated hydrocarbon diluent stream, and hydrogen may be fed to a catalytic distillation reactor system for concurrently separating linear C5 olefins from saturated hydrocarbon diluent, cyclic C5 olefins, and C5 dienes contained in the second fraction and selectively hydrogenating C5 dienes. An overhead distillate including the linear C5 olefins and a bottoms product including cyclic C5 olefins are recovered from the catalytic distillation reactor system. Other aspects of the C5
(Continued)

olefin systems and processes, including catalyst configurations and control schemes, are also described.

7 Claims, 18 Drawing Sheets

Related U.S. Application Data of application No. 15/901,261, filed on Feb. 21, 2018, now Pat. No. 10,252,240, which is a division of application No. 15/010,173, filed on Jan. 29, 2016, now Pat. No. 10,035,125.

(60) Provisional application No. 62/109,263, filed on Jan. 29, 2015, provisional application No. 62/109,289, filed on Jan. 29, 2015, provisional application No. 62/109,272, filed on Jan. 29, 2015, provisional application No. 62/109,279, filed on Jan. 29, 2015.

(51) Int. Cl.
| | |
|---|---|
| *C07C 7/05* | (2006.01) |
| *C07C 7/163* | (2006.01) |
| *C07C 7/167* | (2006.01) |
| *C07C 7/177* | (2006.01) |
| *C10G 45/32* | (2006.01) |
| *C10G 50/00* | (2006.01) |
| *C10G 9/36* | (2006.01) |
| *B01J 8/00* | (2006.01) |
| *B01J 8/04* | (2006.01) |
| *C07C 5/03* | (2006.01) |
| *C10G 45/36* | (2006.01) |
| *C07C 5/08* | (2006.01) |
| *C10G 45/40* | (2006.01) |

(52) U.S. Cl.
CPC .......... *C07C 5/08* (2013.01); *C07C 6/04* (2013.01); *C07C 7/05* (2013.01); *C07C 7/163* (2013.01); *C07C 7/167* (2013.01); *C07C 7/177* (2013.01); *C10G 9/36* (2013.01); *C10G 45/32* (2013.01); *C10G 45/36* (2013.01); *C10G 45/40* (2013.01); *C10G 50/00* (2013.01); *B01J 2208/00584* (2013.01); *B01J 2208/00628* (2013.01); *B01J 2219/00006* (2013.01); *Y02P 20/127* (2015.11); *Y02P 20/52* (2015.11)

(56) References Cited

U.S. PATENT DOCUMENTS

| | | |
|---|---|---|
| 6,410,811 B2 | 6/2002 | Chau et al. |
| 2003/0094245 A1 | 5/2003 | Akita et al. |
| 2004/0019245 A1 | 1/2004 | Gartside et al. |
| 2014/0018584 A1* | 1/2014 | Xu .................... C07C 7/163 |
| | | 585/251 |

OTHER PUBLICATIONS

Office Action with Search Report issued in corresponding Chinese Application No. 201680019603.3, dated May 1, 2020 (16 pages).

* cited by examiner

PRODUCING C5 OLEFINS FROM STEAM CRACKER C5 FEEDS—A PROCESS USING A CATALYTIC DISTILLATION REACTOR SYSTEM

CROSS-REFERENCE TO RELATED APPLICATIONS

This application, pursuant to 35 U.S.C. § 119(e), claims benefit to U.S. Provisional Application Ser. Nos. 62/109,263, 62/109,272, 62/109,279, and 62/109,289, all of which were filed Jan. 29, 2015. These applications are incorporated herein by reference in their entirety.

BACKGROUND

Crude streams for the commercial production of olefins contain various compounds as impurities. Acetylenic and diene impurities need to be removed from the streams to produce acceptable quality olefin products. To produce olefins such as ethylene, propylene, butene, pentene and the like, acetylenic impurities such as acetylene, methyl acetylene, vinyl acetylene, ethyl acetylene, 2-methyl-1-buten-3-yne and the like, as well as diene compounds, such as butadiene, propadiene, and the like, in various crude mixed C2-C5 streams need to be removed with minimum loss of useful materials such as ethylene, propylene, butene, pentene, and the like in the feed streams. The preferred technique for the purification in commercial practice is the selective hydrogenation of acetylenic and diene compounds over hydrogenation catalysts.

Crude C5 olefin-containing streams may include various dienes and acetylenes, which often must be removed before use of the C5 olefin-containing stream in downstream processing units, such as a downstream metathesis unit. In addition to the need to remove dienes and acetylenes, which produce coke and shorten metathesis catalyst run length, cyclopentene must also be removed from the C5 feed to a very low level, such as less than 0.5 wt %, 1.5 wt %, or 2.5 wt %, as cyclopentene may undergo undesirable ring-opening metathesis polymerization in the downstream metathesis unit.

Various feeds may be used to provide the C5 olefins, including C5 fractions from crackers, such as a fluid catalytic cracker (FCC) or a steam cracker. The mixed C5's from such crackers is typically processed to result in feed of only the desired C5's, with minimal impurities, to the metathesis unit. For example, C5's from an FCC unit may be fed to a selective hydrogenation unit and fractionated to separate the C6+ hydrocarbons and cyclic C5 olefins from linear and iso C5 olefins, which may then be used in a metathesis process.

Such a simple system may not be suitable for steam cracker C5 products, however. Steam cracking processes produce C5 hydrocarbon streams having a very high concentration of cyclopentadiene and dicyclopentadiene, in addition to linear C5 dienes, isoolefins, and acetylenes, relative to FCC C5 products. The higher diene content, for example, if processed similar to an FCC C5 product, may result in high rates of catalyst fouling and potential runaway reactions. Further, sulfur compounds present in the C5 feed could potentially inhibit/damage the catalyst performance.

U.S. Pat. No. 3,492,220 to Lempert et al., 1970, disclosed a process for hydrotreating a full boiling-range pyrolysis gasoline containing styrene and C5 and lighter hydrocarbons with a sulfided nickel catalyst under conditions that produce either stable gasoline in a single zone or a substantially olefin-free, sulfur-free product in two or more reaction zones. However, this disclosed process is not selective to olefins.

U.S. Pat. No. 3,691,066 to Carruthers et al., 1972, disclosed a supported nickel catalyst for selective hydrogenation of unsaturated gasolines, e.g. steam cracker gasoline. The diene content is reduced from 4-55% wt to below 0.5% wt. Total sulphur content of the feedstock is 0.1-1.5% wt., of which 0.003-1.0% wt. may be thiophenic sulphur. Runs of over 500 hours, particularly over 1000 hours were noted are possible. It was stated therein that fresh wholly elemental nickel catalyst is not selective in its hydrogenation activity and will hydrogenate mono and diolefins and aromatics and the fact that monoolefins and aromatics remain unhydrogenated in the present process is due to the partial sulphiding of the nickel catalyst by the thiophenic sulphur normally present in the feedstock.

U.S. Pat. No. 4,059,504 to Bauer, 1977, disclosed a process in which pyrolysis gasoline is stabilized by hydrotreating in the presence of a catalyst of cobalt-tungsten sulfide supported on high surface area alumina. It was stated in this patent that the non-noble catalysts, the most widely used being Ni, W—Ni, Ni—Mo and Co—Mo, supported on a high-surface alumina base, require either pre-sulfidation or operation with high sulfur content feeds. It was also noted that the non-noble metal catalysts heretofore used in the art have the disadvantage in that they tend to produce polymers during the hydrotreating. In this patent, the active form of the catalyst is the sulfide form, and the catalyst is preferably pre-sulfided, although when using high sulfur feeds, the active sulfide form is produced on-stream, whereby, in some cases, pre-sulfiding is not required.

EP0011906 to Christy et al., 1983, disclosed a process for the selective hydrogenation of dienes in pyrolysis gasoline which includes catalytic hydrogenation of the pyrolysis gasoline in at least three consecutive reactors. In at least two of the consecutive reactors, the process includes recirculating part of the hydrocarbon mixture emerging from a reactor over that reactor. The catalyst used for the catalytic hydrogenation comprises partially sulfided nickel on alumina as a support. The weight ratio of hydrocarbon mixture recirculated to the first reactor and the pyrolysis gasoline fed thereto is from 5 to 15 and to the second reactor from 2 to 4. The examples provided show the unsaturate recovery (dienes+olefins) for the first case is 91.27% and for the second case is 87.79%, with 5000 dienes ppm remaining in the product stream.

U.S. Pat. No. 6,686,309 ('309) to Didillon et al, 2004, disclosed a palladium based catalyst, with at least one metal selected from molybdenum and tungsten, in the form of at least one oxide, for selective hydrogenation of unsaturated diolefinic compounds in gasolines without hydrogenating the aromatic and mono-olefinic compounds. In the background of the '309 patent, it was acknowledged that two main types of catalyst are generally used for hydrogenating diolefins and styrenic compounds: catalysts using noble group VIII metals such as palladium, and those using non-noble group VIII metals such as nickel. It was stated that the second type of catalyst generally has a lower activity and undesired oligomerizing properties, which necessitates frequent regeneration and the use of a distillation column after hydrogenation to eliminate the heavy compounds. Further, such catalysts were noted as useful to only treat feeds containing large quantities of mercaptans, such as that found in catalytic cracking gasolines.

CN101254465 A (Sinopec) disclosed a selective hydrogenation catalyst for cracking C5 streams, which contains the following components in the given mass percentages: Ni 10-35%, La 0.5-3%, Ag 0.3-3% and aluminum oxide carrier 59-89.2%, and can contain other metals. Metal La and precious metal Ag are claimed to be required to improve catalyst selectivity and resistance to carbon deposition. It is stated that since cracking C5 fraction containing a lot of dienes is easy to generate a polymer which will cover the active sites of the catalyst and reduce catalyst activity, adding an alkaline or alkaline earth metal catalyst will be good to reduce the formation of polymers.

SUMMARY OF THE CLAIMED EMBODIMENTS

Embodiments disclosed herein relate generally to processes and systems for the production of linear C5 olefins from steam cracker C5 feeds. The processes and systems disclosed herein have been found useful for treating and separating steam cracker C5 hydrocarbons such that the olefins recovered from the steam cracker C5 hydrocarbons may be used in downstream processes, such as in a downstream metathesis unit for the production of propylene, for example.

In one aspect, embodiments disclosed herein relate to a process for producing C5 olefins from a steam cracker C5 feed. The process may include reacting a mixed hydrocarbon stream comprising cyclopentadiene, linear C5 olefins, cyclic C5 olefins, and C6+ hydrocarbons wherein cyclopentadiene is dimerized to form dicyclopentadiene. The reacted mixture may then be separated in a fractionator to form a first fraction comprising the C6+ hydrocarbons and dicyclopentadiene and a second fraction comprising the linear and cyclic C5 olefins and C5 dienes. The second fraction and hydrogen may then be fed to a catalytic distillation reactor system, wherein the second fraction is introduced intermediate a first catalyst zone and a second catalyst zone. Concurrently in the catalytic distillation reactor system: the linear C5 olefins are separated from the cyclic C5 olefins and C5 dienes contained in the second fraction; and at least a portion of the C5 dienes are selectively hydrogenated to form additional C5 olefins. An overhead distillate including the linear C5 olefins and a bottoms product including cyclic C5 olefins are recovered from the catalytic distillation reactor system.

In another aspect, embodiments disclosed herein relate to a process for producing C5 olefins from a steam cracker C5 feed. The process may include reacting a mixed hydrocarbon stream comprising cyclopentadiene, linear C5 olefins, cyclic C5 olefins, and C6+ hydrocarbons in a dimerization reactor wherein cyclopentadiene is dimerized to form dicyclopentadiene, producing a dimerization reactor effluent. The dimerization reactor effluent may then be separated in a fractionator to form a first fraction comprising the C6+ hydrocarbons and dicyclopentadiene and a second fraction comprising the linear and cyclic C5 olefins and C5 dienes. The second fraction, a saturated hydrocarbon diluent stream, and hydrogen may then be fed to a catalytic distillation reactor system, wherein the second fraction is introduced intermediate a first catalyst zone and a second catalyst zone. Concurrently in the catalytic distillation reactor system: the linear C5 olefins are separated from the saturated hydrocarbon diluent, the cyclic C5 olefins, and C5 dienes contained in the second fraction; and at least a portion of the C5 dienes are selectively hydrogenated to form additional C5 olefins. An overhead distillate including the linear C5 olefins and a bottoms product including cyclic C5 olefins are recovered from the catalytic distillation reactor system.

The process may further include: purging a portion of the bottoms product; reacting a remaining portion of the bottoms product in a total hydrogenation unit to convert the cyclic C5 olefins to cyclopentane; and recycling the cyclopentane to the catalytic distillation reactor system as the saturated hydrocarbon diluent. In some embodiments, the saturated hydrocarbon diluent may include one or more hydrocarbons having a normal boiling point of at least 102.5° F.

The process may also include feeding the overhead distillate from the catalytic distillation reactor system to a metathesis unit and converting the linear C5 olefins to propylene. The overhead distillate may include less than 2.5 wt % cyclopentene, and the second fraction may include less than 0.5 wt % benzene, in various embodiments. An olefin recovery, measured as moles linear and branched C5 olefins in the overhead distillate divided by moles linear and branched C5 olefins and dienes in the mixed hydrocarbon stream, may be greater than 80%, such as greater than 83%.

The process may include, in various embodiments: operating the dimerization reactor at a pressure in the range from about 130 psia to about 170 psia and a temperature in the range from about 210° F. to about 250° F.; operating the fractionator at a pressure in the range from about 15 psia to about 85 psia and at a condenser temperature in the range from about 97° F. and 213° F.; operating the catalytic distillation reactor system at a pressure in the range from about 60 psia to about 240 psia and a reboiler temperature in the range from 220° F. and 320° F., and a hydrogen partial pressure in the range from about 1 psi to about 25 psia; and operating the total hydrogenation unit at a pressure in the range from about 220 psia to about 300 psia and at a temperature in the range from about 200° F. and 260° F.

The mixed hydrocarbon stream may also contain sulfur compounds, which may be recovered in the first fraction. The process may also include partially vaporizing the second fraction prior to introducing the second fraction to the catalytic distillation reactor system. The partial vaporizer may be operated at conditions sufficient to vaporize between 5 wt % and 95 wt % of the C5 dienes. In other embodiments, the process further includes separating the overhead distillate to recover a product fraction comprising linear C5 olefins and a recycle fraction comprising cyclopentene.

In another aspect, embodiments disclosed herein relate to a process for producing C5 olefins from a steam cracker C5 feed. The process may include reacting a mixed hydrocarbon stream comprising cyclopentadiene, linear C5 olefins, cyclic C5 olefins, and C6+ hydrocarbons in a dimerization reactor wherein cyclopentadiene is dimerized to form dicyclopentadiene, producing a dimerization reactor effluent. The dimerization reactor effluent may then be separated in a fractionator to form a first fraction comprising the C6+ hydrocarbons and dicyclopentadiene and a second fraction comprising the linear and cyclic C5 olefins and linear C5 dienes. The second fraction, a saturated hydrocarbon diluent stream, and hydrogen are fed to a catalytic distillation reactor system, wherein the second fraction is introduced below a first catalyst zone. Concurrently in the catalytic distillation reactor system: the linear C5 olefins are separated from the saturated hydrocarbon diluent, the cyclic C5 olefins, and linear C5 dienes contained in the second fraction; and at least a portion of the C5 dienes are selectively hydrogenating to form additional linear C5 olefins. An overhead distillate including the linear C5 olefins and a bottoms product including cyclic C5 olefins are recovered from the catalytic distillation reactor system.

The process may further include purging a portion of the bottoms product; reacting a remaining portion of the bottoms product in a total hydrogenation unit to convert the cyclic C5 olefins to cyclopentane; and recycling the cyclopentane to the catalytic distillation reactor system as the saturated hydrocarbon diluent. In some embodiments, the process further includes feeding the second fraction to a fixed bed selective hydrogenation unit to selectively hydrogenate C5 dienes prior to feeding the second fraction to the catalytic distillation reactor system. The second fraction may be partially vaporized prior to introducing the second fraction to the catalytic distillation reactor system, and the overhead distillate may be separated to recover a product fraction comprising linear C5 olefins and a recycle fraction comprising cyclopentene.

In another aspect, embodiments disclosed herein relate to a process for producing C5 olefins from a mixed C5 feed. The process may include feeding hydrogen and a mixed hydrocarbon stream comprising cyclopentadiene, linear C5 olefins, cyclic C5 olefins, and C6+ hydrocarbons to a catalytic distillation reactor system. Concurrently in the catalytic distillation reactor system: the linear C5 olefins are separated from the cyclic C5 olefins, C5 dienes, and C6+ hydrocarbons; and at least a portion of the C5 dienes are selectively hydrogenating to form additional linear C5 olefins. A liquid side draw is withdrawn from a stage below a mixed hydrocarbon feed location and a hydrogen feed location and above a main reboiler, at least partially vaporizing the liquid side draw in an intermediate reboiler, and returning the at least partially vaporized liquid side draw to the catalytic distillation reactor system. An overhead distillate including the linear C5 olefins and a bottoms product including cyclic C5 olefins are recovered from the catalytic distillation reactor system. In some embodiments, the main reboiler of the catalytic distillation reactor system may be operated at a temperature of less than about 302° F.

In another aspect, embodiments disclosed herein relate to a process for the selective hydrogenation of C5 dienes in a mixed C5 hydrocarbon stream. The process may include feeding hydrogen and a C5-olefin containing stream containing linear pentenes, dienes, acetylenes, and a diluent compound to a catalytic distillation reactor system. Concurrently in the catalytic distillation reactor system, the acetylenes and dienes may be hydrogenated, and the C5-olefin containing stream may be fractionated to recover an overheads fraction comprising the pentenes and a bottoms fraction. The catalytic distillation reactor system may have at least three reaction zones, including: a first reaction zone disposed below a C5-olefin containing stream feed elevation and containing a nickel-based catalyst; a second reaction zone disposed above the C5-olefin containing stream feed elevation and containing a nickel-based catalyst; and a third reaction zone disposed above the second reaction zone and containing a palladium-based catalyst.

In another aspect, embodiments disclosed herein relate to a process for producing C5 olefins from a steam cracker C5 feed. The process may include reacting a mixed hydrocarbon stream comprising cyclopentadiene, linear C5 olefins, cyclic C5 olefins, and C6+ hydrocarbons in a dimerization reactor wherein cyclopentadiene is dimerized to form dicyclopentadiene, producing a dimerization reactor effluent. The dimerization reactor effluent may then be separated in a fractionator to form a first fraction comprising the C6+ hydrocarbons and dicyclopentadiene and a second fraction comprising the linear and cyclic C5 olefins and C5 dienes. The second fraction, a saturated hydrocarbon diluent stream, and hydrogen may be fed to a catalytic distillation reactor system, which may have at least three reaction zones, including a first reaction zone disposed below a C5-olefin containing stream feed elevation and containing a nickel-based catalyst, a second reaction zone disposed above the C5-olefin containing stream feed elevation and containing a nickel-based catalyst, and a third reaction zone disposed above the second reaction zone and containing a palladium-based catalyst. Concurrently in the catalytic distillation reactor system: the linear C5 olefins may be separated from the saturated hydrocarbon diluent, the cyclic C5 olefins, and C5 dienes contained in the second fraction, and at least a portion of the C5 dienes may be selectively hydrogenated to form additional C5 olefins. An overhead distillate including the linear C5 olefins may be recovered from the catalytic distillation reactor system. A bottoms product including cyclic C5 olefins may also be recovered from the catalytic distillation reactor system.

The process may further include: purging a portion of the bottoms product;

reacting a remaining portion of the bottoms product in a total hydrogenation unit to convert the cyclic C5 olefins to cyclopentane; and recycling the cyclopentane to the catalytic distillation reactor system as the saturated hydrocarbon diluent. The saturated hydrocarbon diluent may be one or more hydrocarbons having a normal boiling point of at least 102.5° F. The process may also include feeding the overhead distillate from the catalytic distillation reactor system to a metathesis unit and converting the linear C5 olefins to propylene.

In some embodiments, the overhead distillate may contain less than 2.5 wt % cyclopentene, and the second fraction may contain less than 0.5 wt % benzene. An olefin recovery, measured as linear and branched C5 olefins in the overhead distillate divided by linear and branched C5 olefins and dienes in the mixed hydrocarbon stream, may be greater than 92.5 wt %, such as greater than 95 wt %.

The process may include: operating the dimerization reactor at a pressure in the range from about 130 psia to about 170 psia and a temperature in the range from about 210° F. to about 250° F.; operating the fractionator at a pressure in the range from about 15 psia to about 85 psia and at a condenser temperature in the range from about 97° F. and 213° F.; operating the catalytic distillation reactor system at a pressure in the range from about 60 psia to about 240 psia and a reboiler temperature in the range from 220° F. and 320° F., and a hydrogen partial pressure in the range from about 1 psi to about 25 psia; and operating the total hydrogenation unit at a pressure in the range from about 220 psia to about 300 psia and at a temperature in the range from about 200° F. and 260° F. The process may further include separating the overhead distillate to recover a product fraction comprising linear C5 olefins and a recycle fraction comprising cyclopentene.

The nickel-based catalyst may contain from about 5 wt % to about 30 wt % nickel. The nickel-based catalyst may be disposed on a diatomaceous earth support, have a BET surface area in the range from about 20 m$^2$/g to about 400 m$^2$/g, and have a pore volume in the range from about 0.2 ml/g to about 0.7 ml/g. The palladium-based catalyst may contain from about 0.2 to about 1.0 wt % palladium disposed on an alumina support.

In another aspect, embodiments disclosed herein relate to a system for producing C5 olefins from a mixed C5 hydrocarbon feedstock. The system may include a catalytic distillation reactor system for concurrently converting C5 dienes to C5 olefins and separating the mixed C5 hydrocarbon feedstock into an overheads olefin product and a bottoms product. The catalytic distillation reactor system may have at least three reaction zones, including: a first reaction zone disposed below a C5-olefin containing stream feed elevation and containing a nickel-based catalyst; a second reaction zone disposed above the C5-olefin containing stream feed elevation and containing a nickel-based catalyst; and a third reaction zone disposed above the second reaction zone and containing a palladium-based catalyst.

The system may further include: a dimerization reactor for converting cyclopentadiene in a mixed hydrocarbon to dicyclopentadiene and producing a dimerization reactor effluent; and a separator for separating the dimerization reactor effluent to form a bottoms fraction including the dicyclopentadiene and an overheads fraction comprising the mixed C5 hydrocarbon feedstock. The system may also include a total hydrogenation reactor for converting cyclopentene in the bottoms product to cyclopentane. A flow conduit may also be provided for recycling an effluent from the total hydrogenation reactor to the catalytic distillation reactor system.

In another aspect, embodiments disclosed herein relate to a process for the selective hydrogenation of C5 dienes in a mixed C5 hydrocarbon stream. The process may include: feeding hydrogen and a C5-olefin containing stream comprising linear pentenes, dienes, acetylenes, and a diluent compound to a catalytic distillation reactor system. Concurrently in the catalytic distillation reactor system, the acetylenes and dienes may be hydrogenated, and the C5-olefin containing stream may be fractionated to recover an overheads fraction comprising the pentenes and a bottoms fraction. The process may further include determining a concentration of the diluent compound at one or more column elevations, and adjusting one or more column operating parameters to maintain a set point concentration or a concentration profile of the diluent compound at the one or more column elevations.

The catalytic distillation reactor system may include an upper catalyst zone above a C5-olefin containing stream feed elevation and a lower catalyst zone below the C5-olefin containing stream feed elevation. The process may further include at least one of: measuring a concentration of the diluent compound at an elevation below the lower catalyst zone; measuring a concentration of the diluent compound at an elevation intermediate the upper and lower catalyst zones; or measuring a concentration of the diluent compound at an elevation above the upper catalyst zone. Alternatively or additionally, the process may include at least one of: measuring a density of a liquid fraction at an elevation below the lower catalyst zone and determining the concentration of the diluent compound at the elevation below based upon the measured density; measuring a density of a liquid fraction at an elevation intermediate the upper and lower catalyst zones and determining the concentration of the diluent compound at the elevation intermediate based upon the measured density; or measuring a density of a liquid fraction at an elevation above the upper catalyst zone and determining the concentration of the diluent compound at the elevation above based upon the measured density.

The diluent compound may include cyclopentane, cyclopentene, or a combination thereof. In some embodiments, the diluent compound comprises one or more hydrocarbons having a normal boiling point in the range from about 100° F. to about 125° F. In various embodiments, the diluent compound comprises one or more hydrocarbons having a specific gravity in the range from about 0.7 to about 0.8.

In some embodiments, a sample elevation (the elevation at which a sample is withdrawn from the column) used in the determining step is disposed proximate an elevation of maximum rate of change in concentration of the diluent compound within the catalytic distillation reactor system. The process may further include determining an elevation of maximum rate of change in concentration of the diluent compound within the catalytic distillation reactor system.

The adjusting step may include at least one of: decreasing an overhead flow and increasing a reflux flow when a diluent compound concentration profile starts to move up the column and the reflux flow is below a column flooding value; increasing an overhead flow and decreasing reflux flow when a diluent compound concentration profile starts to move down the column and the reflux flow is above a minimum design value; decreasing a reboiler duty and an overhead flow when the diluent compound concentration profile starts to move up the column; or increasing a reboiler duty and an overhead flow when the diluent compound concentration profile starts to move down the column.

In another aspect, embodiments disclosed herein relate to a process for the selective hydrogenation of C5 dienes in a mixed C5 hydrocarbon stream. The process may include: feeding hydrogen and a C5-olefin containing stream comprising linear pentenes, dienes, acetylenes, cyclopentane and cyclopentene to a catalytic distillation reactor system, and concurrently in the catalytic distillation reactor system: hydrogenating the acetylenes and dienes, and fractionating the C5-olefin containing stream. An overheads fraction comprising the pentenes may be recovered from the catalytic distillation reactor system, as may be a bottoms fraction. The process may also include determining a density of a liquid fraction at one or more column elevations, and adjusting one or more column operating parameters to maintain a set point density or density profile at the one or more column elevations.

The catalytic distillation reactor system may include an upper catalyst zone above a C5-olefin containing stream feed elevation and a lower catalyst zone below the C5-olefin containing stream feed elevation. In such embodiments, the process may include at least one of: measuring a density of the liquid fraction at an elevation below the lower catalyst zone; measuring a density of the liquid fraction at an elevation intermediate the upper and lower catalyst zones; or measuring a density of the liquid fraction at an elevation above the upper catalyst zone. The process may further comprising estimating a concentration of at least one of cyclopentene and cyclopentane in the liquid fraction(s) based upon the measured density(ies).

The adjusting may include at least one of: decreasing an overhead flow and increasing a reflux flow when a density profile indicates a concentration of a target compound is starting to move up the column and the reflux flow is below a column flooding value; increasing an overhead flow and decreasing reflux flow when a density profile indicates a concentration of a target compound is starting to move down the column and the reflux flow is above a minimum design value; decreasing a reboiler duty and an overhead flow when the density profile indicates a concentration of a target compound is starting to move up the column; or increasing a reboiler duty and an overhead flow when the density profile indicates a concentration of a target compound is starting to move down the column. The target compound may include cyclopentane, cyclopentene, or a combination thereof. The diluent compound may include one or more hydrocarbons having a normal boiling point in the range from about 100° F. to about 125° F., and in some embodiments the diluent compound comprises one or more hydrocarbons having a specific gravity in the range from about 0.7 to about 0.8.

In another aspect, embodiments disclosed herein relate to a method for controlling a catalytic distillation reactor system, including: feeding one or more reactants and an inert compound to a catalytic distillation reactor system having one or more reaction zones; concurrently in the catalytic distillation reactor system: converting the reactants to one or more products; and fractionating the reactants and products; recovering an overheads fraction; recovering a bottoms fraction. A concentration of the inert compound may be determined at one or more column elevations, and one or more column operating parameters may be adjusted to maintain a set point concentration or a concentration profile of the inert compound at the one or more column elevations.

In another aspect, embodiments disclosed herein relate to a system for producing C5 olefins from a mixed C5 hydrocarbon feedstock. The system may include: a catalytic distillation reactor system, including one or more reaction zones, for concurrently converting C5 dienes to C5 olefins and separating the C5 hydrocarbon feedstock into an overheads olefin product and a bottoms product. The system may also include an analyzer for determining a density profile or a composition profile of a diluent compound within the catalytic distillation reactor system, as well as a controller configured to adjust one or more operating paramenters to maintain a set point density profile or composition profile of the diluent compound within the catalytic distillation reactor system. In some embodiments, the analyzer is a density measurement device, and the controller may be configured to convert a measured density to an estimated composition. The analyzer may be configured to measure the density or composition at an elevation below a feed elevation of the mixed hydrocarbon feedstock, and may also be configured to measure the density or composition at a sample elevation proximate an elevation of maximum rate of change in concentration of the diluent compound within the catalytic distillation reactor system.

In another aspect, embodiments disclosed herein relate to a process for producing C5 olefins from a steam cracker C5 feed, the process including: feeding a mixed hydrocarbon stream comprising cyclopentadiene, linear C5 olefins, cyclic C5 olefins, C5 dienes, and C6+ hydrocarbons to a low temperature/low pressure (LT/LP) distillation column. Concurrently in the LT/LP distillation column, the cyclopentadiene may be reacted to form a dimerized product comprising dicyclopentadiene, and the mixed hydrocarbon stream may be separated to form a first fraction comprising the C6+ hydrocarbons and dicyclopentadiene and a second fraction comprising the linear and cyclic C5 olefins and C5 dienes. The second fraction and hydrogen may be fed to a catalytic distillation reactor system, wherein the second fraction is introduced intermediate a first catalyst zone and a second catalyst zone. Concurrently in the catalytic distillation reactor system, the linear C5 olefins may be separated from the cyclic C5 olefins and C5 dienes contained in the second fraction, and at least a portion of the C5 dienes may be selectively hydrogenated to form additional C5 olefins. An overhead distillate comprising the linear C5 olefins and a bottoms product comprising cyclic C5 olefins may be recovered from the catalytic distillation reactor system.

The low temperature/low pressure distillation column, in some embodiments, may be operated in liquid continuous distillation operation. A saturated hydrocarbon diluent stream may also be co-fed with the second fraction and hydrogen to the catalytic distillation reactor system. The process may further include: purging a portion of the bottoms product; reacting a remaining portion of the bottoms product in a total hydrogenation unit to convert the cyclic C5 olefins to cyclopentane; and recycling the cyclopentane to the catalytic distillation reactor system as the saturated hydrocarbon diluent. The total hydrogenation unit may be operated, for example, at a pressure in the range from about 220 psia to about 300 psia and at a temperature in the range from about 200° F. and 260° F. An average residence time in the low temperature/low pressure distillation column may be in the range from 0.2 hours to 6 hours, such as a residence time is sufficient to allow for greater than 90 wt % of the cyclopentadiene to dimerize. In some embodiments, the low temperature/low pressure distillation column may be operated at a pressure in the range from about 15 psia to about 85 psia, at an overhead condenser temperature in the range from about 90° F. to about 150° F., and at a reboiler temperature in the range from about 155° F. to 300° F.

In another aspect, embodiments disclosed herein relate to a system for producing C5 olefins from a steam cracker C5 feed. The system may include a low temperature/low pressure distillation column configured to concurrently (a) fractionate a mixed hydrocarbon stream comprising cyclopentadiene, linear C5 olefins, cyclic C5 olefins, C5 dienes, and C6+ hydrocarbons to recover an overhead distillate comprising linear and cyclic C5 olefins and C5 dienes, and (b) dimerize the cyclopentadiene. The system may also include a catalytic distillation reactor system configured to concurrently (a) separate the linear C5 olefins from the cyclic C5 olefins and C5 dienes in the overhead distillate and (b) selectively hydrogenate at least a portion of the C5 dienes in the overhead distillate to form additional C5 olefins. In some embodiments, the system may also include a total hydrogenation unit configured to convert the cyclic C5 olefins recovered as a bottoms product from the catalyst distillation reactor system to cyclopentene, as well as a metathesis reactor configured to covert the linear C5 olefins recovered from the catalyst distillate reactor system into propylene.

In another aspect, embodiments disclosed herein relate to a process for producing olefins including: feeding a mixed hydrocarbon stream comprising cyclopentadiene, linear C5 olefins, cyclic C5 olefins, C5 dienes, and C6+ hydrocarbons to a low temperature/low pressure distillation column operating in liquid continuous mode. Concurrently in the low temperature/low pressure distillation column, the cyclopentadiene may be reacted to form a dimerized product comprising dicyclopentadiene, and the mixed hydrocarbon stream may be fractionated to form a first fraction comprising the C6+ hydrocarbons and dicyclopentadiene and a second fraction comprising the linear and cyclic C5 olefins and C5 dienes. The process may further include operating the low temperature/low pressure distillation column at a pressure in the range from about 15 psia to about 85 psia, at an overhead condenser temperature in the range from about 90° F. to about 150° F., and at a reboiler temperature in the range from about 155° F. to 300° F. An average residence time in the low temperature/low pressure distillation column may be in the range from 0.2 hours to 6 hours, and the residence time may be sufficient to allow for greater than 90 wt % of the cyclopentadiene to dimerize.

In yet another aspect, embodiments disclosed herein relate to systems for performing the processed described herein. Other aspects and advantages will be apparent from the following description and the appended claims.

BRIEF DESCRIPTION OF DRAWINGS

In the figures, like numerals generally represent like parts.

DETAILED DESCRIPTION

Figure 1:
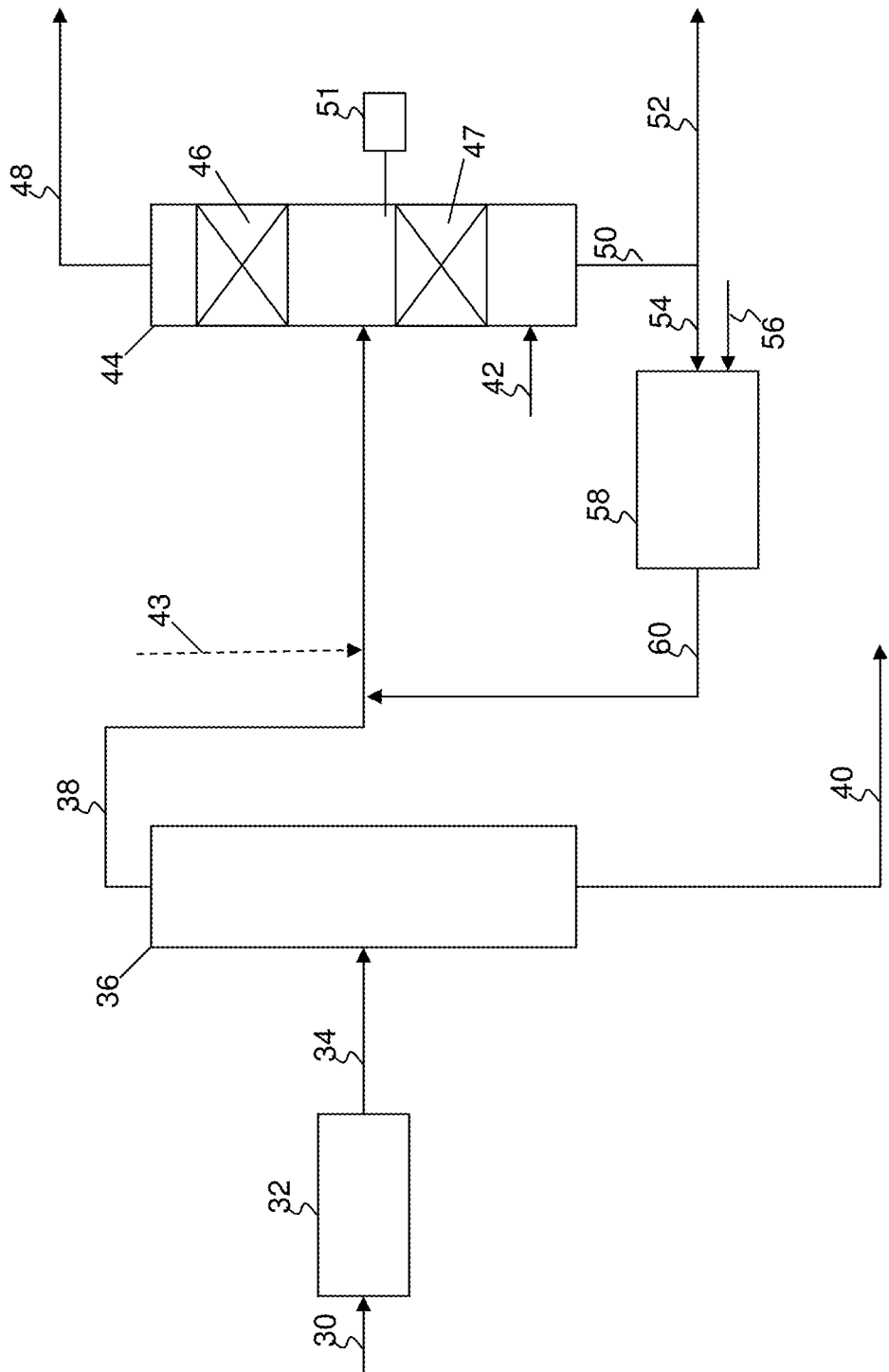
FIGS. 1-5 are simplified flow diagrams of processes to produce C5 olefins according to embodiments disclosed herein.

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

Feed streams according to embodiments disclosed herein may include various refinery streams containing linear and/or iso C5 olefins and various dienes and acetylenic compounds. For example, a C4-C6 cut, a C5 cut, a C5-C6 cut or other various C5 olefin-containing mixtures may be used. In some embodiments, the feed stream is a C5 fraction containing linear pentenes, cyclopentene, as well as linear and/or cyclic diene and/or acetylenic compounds, and may contain C6+ hydrocarbons, such as benzene and toluene, as well as sulfur containing compounds, such as thiophene, 2-methyl thiophene, 3-methyl thiophene, and isobutyl mercaptan, among others. Mixed pentene feedstocks useful in embodiments disclosed herein may include linear pentenes and isopentenes. Mixed pentene feedstocks may also include various other hydrocarbon components, including C4 to C6 paraffins and olefins. In some embodiments, the mixed pentene feedstock may be a C5 hydrocarbon fraction from a steam cracker, where the C5 fraction may include linear pentenes, isopentene, n-pentanes, isopentanes, as well as cyclopentene, cyclopentadiene, linear and branched C5 dienes, and acetylenes.

The steam cracking process produces C5 hydrocarbon streams that may have a relatively high concentration of cyclopentadiene and dicyclopentadiene, as well as other dienes and acetylenes compared to FCC C5 hydrocarbon streams. For example, FCC C5 streams typically contain less than 1 wt % or 2 wt % dienes, whereas steam cracker C5 streams may contain 10% or more dienes, such as 15%, 18%, 25%, or 50% or more dienes. If hydrogenated similar to an FCC C5 product, for example, the additional highly reactive species may result in high rates of catalyst fouling and potential runaway reactions. Furthermore, direct feed of the C5 cut to hydrogenation may result in introducing the sulfur-containing compounds present in the C5 cut to the catalyst zone, which could potentially inhibit or damage the catalyst performance. Cyclopentene concentrations must also be controlled in the desired C5 olefin product, as cyclopentene may undergo undesirable ring-opening metathesis polymerization in a downstream metathesis unit, for example. Additionally, hydrogenation of cyclopentadiene may result in additional cyclopentene formation, which may consume more hydrogen and require significantly higher reflux and reboiler duty to meet overhead cyclopentene specifications.

The above noted problems associated with steam cracker C5 feeds or similar feedstocks containing relatively high amounts of highly reactive species may be addressed by one or more of the processes disclosed herein. Referring initially to FIG. 1, a simplified flow diagram of a process for producing C5 olefins from a mixed hydrocarbon stream 30, such as a steam cracker C5 feed, is illustrated. Mixed hydrocarbon stream 30 may contain cyclopentadiene, linear and branched C5 olefins, linear and branched C5 dienes, cyclic C5 olefins, and C6+ hydrocarbons, among other components as described above.

Mixed hydrocarbon stream 30 may be fed to a selective dimerization reactor 32, which may be a catalytic or non-catalytic reactor. In some embodiments, dimerization reactor 32 may be a heat soaker. In the dimerization reactor, cyclopentadiene is dimerized to form dicyclopentadiene. Additionally, cyclopentadiene may be reacted with other compounds, such as isoprene, to form heavy olefin compounds.

Following dimerization, effluent 34 may be recovered from dimerization reactor 32 and fed to a separator 36. Separator 36 may be a distillation column, fractionator, or any other type of separator useful for separating the dimerization reactor effluent to form a bottoms fraction 40 containing the C6+ hydrocarbons, dicyclopentadiene, and other heavy components, and an overheads fraction 38 containing the linear, branched, and cyclic C5 olefins, and the linear and branched C5 dienes. Any sulfur compounds contained in the mixed hydrocarbon stream may also be recovered with bottoms fraction 40. To obtain the desired separation, separator 36 may be controlled to limit the overhead fraction benzene content to less than 0.5 wt %, for example.

The overhead fraction 38 may then be recovered and fed to a catalytic distillation column reactor 44. Hydrogen 42 and one or more diluent streams 43, 60 may also be fed to catalytic distillation column reactor 44. As illustrated in FIG. 1, catalytic distillation column reactor 44 includes a first catalyst zone 46 and a second catalyst zone 47. Overhead fraction 38 is introduced to catalytic distillation column reactor 44 intermediate first catalyst zone 46 and second catalyst zone 47. Hydrogen 42 may be introduced below the lowest catalyst zone, catalyst zone 47 as illustrated, or may be a split feed having hydrogen introduced below the catalyst zones.

In catalytic distillation reactor system 44, the C5 olefin-containing feed is concurrently fractionated and selectively hydrogenated. The lighter components in the C5 olefin-containing feed traverse up the column, where any acetylenes and dienes boiling up into catalyst zone 46 may be reacted with hydrogen to produce additional olefins and paraffins, before being recovered as an overheads fraction 48. The heavier components in the C5 olefin-containing feed traverse down the column into catalyst zone 47, where acetylenes and dienes may be reacted with hydrogen to produce additional olefins and paraffins. Upon conversion to olefins and paraffins, these lighter boiling components may traverse up the column and be recovered with overheads fraction 48. Heavier boiling components, including unreacted dienes and cyclic olefins, continue to traverse down the column and may be recovered as a bottoms fraction 50. The boiling points of various dienes and olefins are compared in Table 1, illustrating how the selective hydrogenation of dienes in catalyst zone 47 may result in additional production of olefins that may be recovered in the overheads.

TABLE 1

C5 normal boiling point comparison.

| Component | Normal Boiling Point (° F.) |
|---|---|
| Cis-2-pentene | 98.5 |
| Trans-2-pentene | 97.4 |
| Cyclopentene | 111.6 |
| Cyclopentane | 120.65 |
| Cis-1,3-pentadiene | 111.3 |
| 1-trans-3-pentadiene | 107.6 |

The inert solvent or diluent stream added via one or both lines 43, 60 may contain various saturated hydrocarbons, such as linear, branched or cyclic paraffins, boiling in a similar range as the C5 feedstock. Preferably, the diluent may include or only include higher boiling components, such that the diluent may traverse downward from the feed point and be used to dilute the lower portion of column 44, as opposed to the whole of column 44. For example, the inert solvent may include hydrocarbons having a normal boiling point of 102.5° F. or higher, 105° F. or higher, or 107.5° F. or higher, in various embodiments. In this manner, the diluent may help control the reaction of the dienes and cyclic olefins that may preferentially traverse downward into catalyst zone 47. The diluent may also help to wash the catalyst in catalyst zone 47, preventing buildup of polymerized byproducts or coke from the catalyst. In some embodiments, the inert diluent may contain cyclopentane, which boils closer to the C5 dienes than to the desired C5 olefins in the overhead fraction.

In some embodiments, the diluent stream may be provided by hydrogenating the cyclopentene contained in the bottoms fraction 50, as illustrated in FIG. 1. A portion of the bottoms fraction 50 may be purged from the system via stream 52, to control buildup of heavies. A remaining portion of the bottoms fraction 50, including cyclopentene and any unreacted dienes, may be fed via stream 54, along with hydrogen 56, to hydrogenation reactor 58. As it is desired to control cyclopentene content in the column, hydrogenation reactor 58 may be a total hydrogenation unit, feeding excess hydrogen to ensure essentially complete conversion of the cyclopentene and dienes in the bottoms fraction. Any unreacted hydrogen may be carried through effluent 60 into column 44, supplying additional hydrogen for the selective hydrogenation process occurring within upper reaction zone 46.

Overhead distillate fraction 48 recovered from the catalytic distillation reactor system 44, and containing the desirable linear and branched C5 olefins, may then be used in downstream processing. For example, the overhead fraction 48 may be fed to a metathesis unit for converting the linear C5 olefins to propylene.

As mentioned above, it may be desirable to limit the amount of cyclopentene carried over with the overhead product from column 44. Total hydrogenation unit 58 may convert a significant portion of the cyclopentene, however control of the column may be set to limit overhead distillate cyclopentene content to less than 0.5 wt %, less than 1.5 wt % or less than 2.5 wt %, for example.

The dimerization reactor 32 may be operated at a pressure in the range from about 100 psia to about 200 psia, such as from about 130 psia to about 170 psia or from about 140 to about 160 psia, and at a temperature in the range from about 190° F. to about 270° F., such as from about 210° F. to about 250° F. or from about 220° F. to about 240° F. The residence time in the dimerization reactor should be sufficient to convert the cyclopentadiene to dicyclopentadiene, while limiting the thermal reaction of other components, as the dienes may be converted to desirable olefins in column 44, as described above. In some embodiments, the dimerization reaction conditions of temperature, pressure, and residence time are controlled to achieve at least 90% conversion of the cyclopentadiene, such as at least 92%, at least 93%, at least 93% or at least 94% cyclopentadiene conversion to heavier compounds, such as dicyclopentadiene.

Separator 36 may be a low temperature/low pressure separator, such as a fractionator or distillation column operated at a pressure in the range from about 15 psia to about 85 psia, such as from about 20 psia to about 80 psia or from about 25 to about 75 psia, and at a condenser temperature in the range from about 97° F. to about 213° F., such as from about 113° F. to 208° F. or from about 126° F. to about 202° F. As noted above, separator 36 may be controlled, such as via reflux rate and distillate to feed ratio, to minimize the amount of sulfurs and benzene in light fraction 38, and to minimize the amount of valuable olefins and dienes (to be converted to olefins downstream) recovered with heavies fraction 40.

Catalytic distillation reactor system 44 may be operated at a pressure in the range from about 50 psia to about 250 psia, such as from about 60 psia to about 240 psia or from about 70 psia to about 230 psia. To achieve the desired separation and reaction, the system 44 may be operated with a reboiler temperature in the range from about 220° F. to about 320° F., and at a hydrogen partial pressure in the range from about 1 psi to about 25 psi, such as from about 5 psi to about 20 psi. The reboiler duty and reflux rate required may depend on the overhead specification on cyclopentene, and the amount of hydrogen required may depend on the feed concentration of the various dienes, among other variables.

Total hydrogenation unit 58 may be operated at a pressure in the range from about 220 psia to about 300 psia, such as from about 240 psia to about 289 psia and at a temperature in the range from about 200° F. and 260° F., such as a temperature in the range from about 220° F. to about 240° F. To achieve the desired conversion of cyclopentene over a hydrogenation catalyst contained in reactor 58, a hydrogen partial pressure in the range from about 150 psi to about 250 psi may be used, such as a hydrogen partial pressure in the range from about 160 psi to about 200 psi.

The process as illustrated in FIG. 1 may be used to recover a significant portion of the olefins contained in the C5 feedstock. In some embodiments, the process may be operated to achieve a linear olefin recovery, measured as moles C5 olefins in the overhead distillate 48 divided by moles C5 olefins and moles C5 dienes in the mixed hydrocarbon stream 30, of greater than 80%; greater than 82%, greater than 83%, greater than 84%, and greater than 86% in yet other embodiments.

Figure 2:
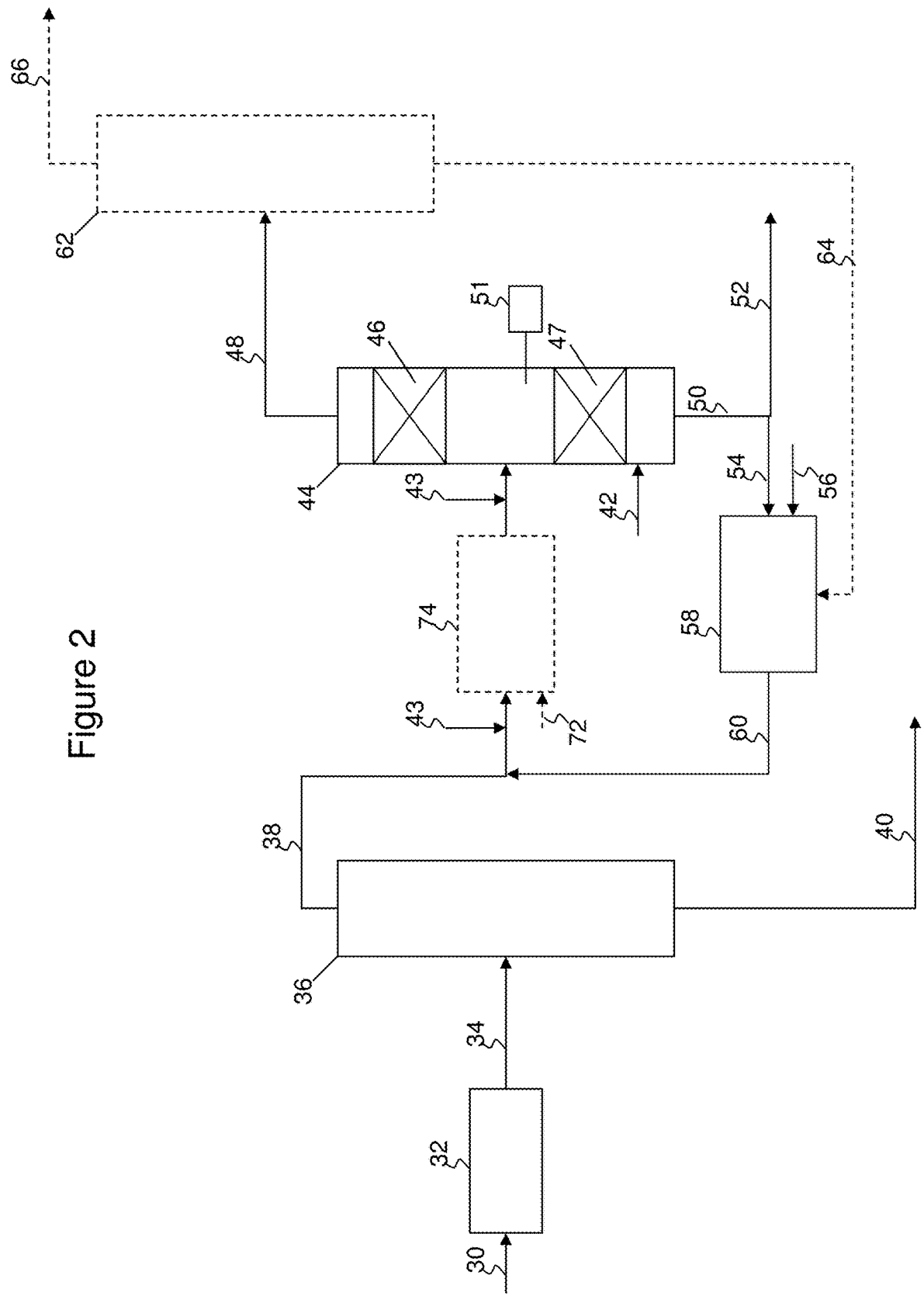

In some embodiments, the process may include a fixed bed selective hydrogenation reactor 74, as shown in FIG. 2, to convert a portion of the dienes in the overhead fraction 38 via reaction with hydrogen 72 prior to introducing the overhead fraction 38 into catalytic distillation reactor system 44. In this manner, the amount of catalyst contained within the distillation column reactor may be reduced or minimized, while achieving the desired selective hydrogenation and separation. In some embodiments, the selective hydrogenation reactor 74 may be in addition to total hydrogenation reactor 58, or may be in lieu of total hydrogenation reactor 58. When used in lieu of total hydrogenation reactor 58, it should be noted that the concentration of cyclopentene within the column may be greater than when the cyclopentene recycle is completely hydrogenated to cyclopentane, and this may affect performance and control of the catalytic distillation reactor system 44.

In other embodiments, the process may include a feed preheater (not shown) intermediate separator 36 and catalytic distillation reactor system 44. The feed preheater may be used to partially vaporize overhead fraction 38 prior to introducing the feed to the catalytic distillation reactor system 44. In this manner, additional dienes may be boiled up into catalyst zone 46, increasing the residence time of the dienes over catalyst in zones 46 and 47. Partial vaporization of the feed may result in additional olefin recovery, or may alternatively be used to reduce reboiler duty requirements to achieve a similar olefin recovery as compared to processes without a feed preheater. For example, the partial vaporizer may be operated at conditions sufficient to vaporize between 5 wt % and 95 wt % of the C5 dienes contained in the feed, such as from about 10 wt % to about 50 wt % of the dienes in the feed.

It has also been found that additional improvements to olefin recovery may be made by loosening the specifications on overheads fraction 48. For example, by allowing additional cyclopentene in the overhead fraction, the losses of olefins to the bottoms product, to meet overhead cyclopentene concentration requirements, may be reduced. Additionally, losses of olefins due to excess conversion in catalyst zones 46, 47 due to increased average residence time (higher reflux ratios, and increased recycle of desired olefins through the column), etc., may also be reduced. Overhead fraction 48 may then be fed to a splitter or separator 62, as illustrated in FIG. 2, to separate a portion of the cyclopentene from the overhead product, resulting in a C5 olefin product stream 66 meeting cyclopentene specifications while improving olefin recovery. The cyclopentene-enriched stream 64 may then be recycled back to total hydrogenation unit 58, as illustrated, or to selective hydrogenation unit 74 when used in lieu of total hydrogenation unit 58.

Figure 3:
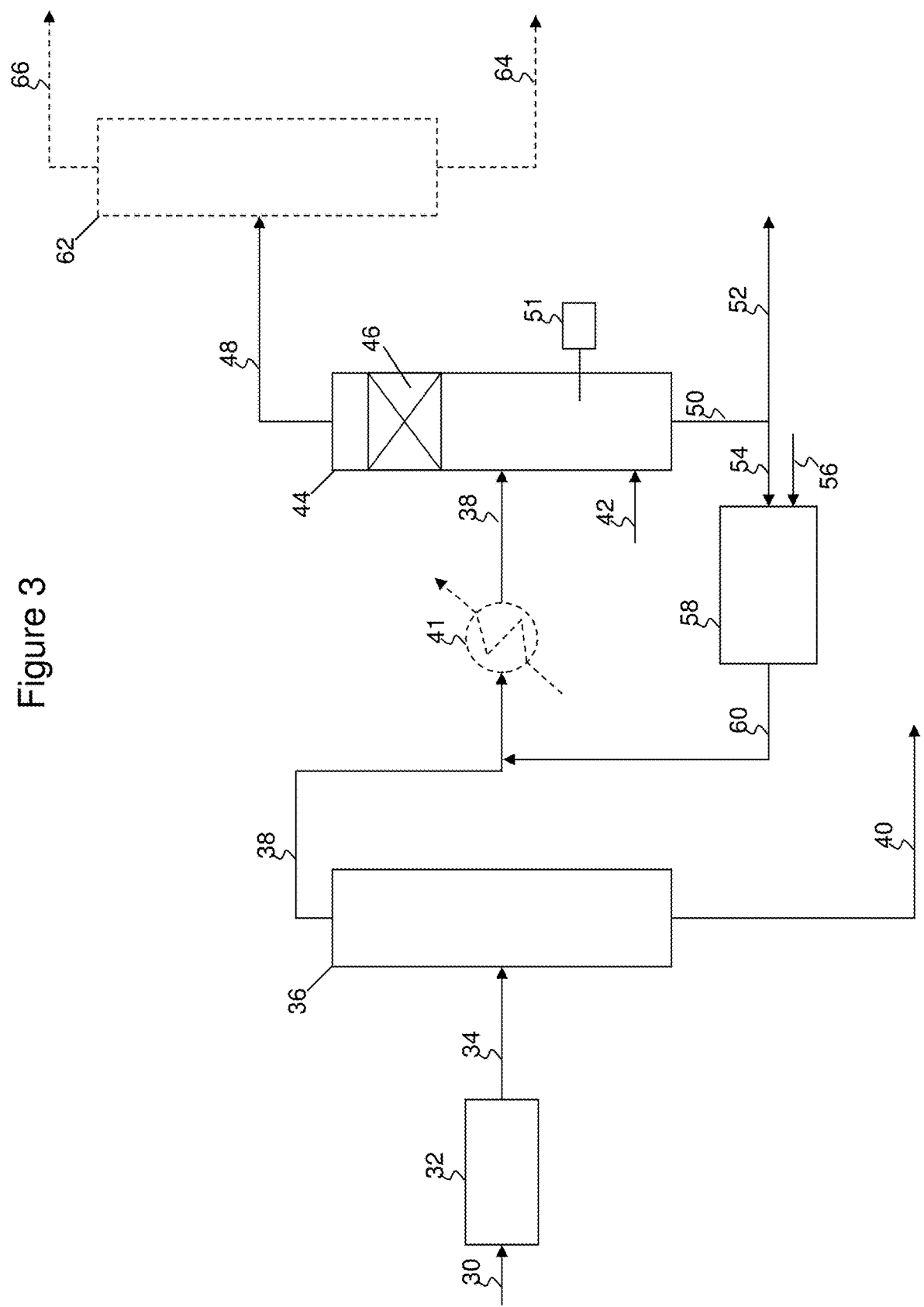

In some embodiments, such as illustrated in FIG. 3, catalytic distillation reactor system 44 may be operated with only a reaction zone located above the location at which overhead fraction 38 is introduced to the column. In column 44, the C5 olefin-containing feed is concurrently fractionated and selectively hydrogenated. The lighter components in the C5 olefin-containing feed traverse up the column, where any acetylenes and dienes may be reacted with hydrogen to produce additional olefins and paraffins, before being recovered as an overheads fraction 48. The heavier components in the C5 olefin-containing feed traverse down the column and are recovered as a bottoms fraction 50.

The process of FIG. 3 may incur olefin losses not incurred by the process of FIG. 1, due to lack of hydrogenation of dienes that may occur over catalyst zone 47 (FIG. 1). However, as described above, partial vaporization of the feed, such as in a feed preheater 41 (FIG. 3), use of a fixed bed selective hydrogenation unit upstream of column 44, or operation of column 44 to increase boilup into column 46 coupled with downstream cyclopentene removal in separator 62, may be used to improve olefin recovery rates, if desired. Use of these alternatives may provide a means to achieve a decent olefin recovery while negating the fouling that may occur in lower catalyst zone 47. The cost/benefit analysis to determine the best operating system may depend upon the type of catalytic distillation reactor system used, the amount, type and replacement frequency of catalyst in catalyst zone 47, as well as the overall feed composition.

Low pressure, low temperature separator 36, as described above with respect to FIG. 1, removes dicyclopentadiene from the mixed hydrocarbons being fed to distillation column reactor system 44. At higher temperatures, such as at temperatures of about 300° F. or greater, dicyclopentadiene may back crack into cyclopentadiene. Introduction of dicyclopentadiene into catalytic distillation reactor system 44 is thus generally not desired, as the dicyclopentadiene may be exposed to relatively high temperatures in the column reboiler, back crack to form cyclopentadiene, which although it may be subsequently hydrogenated to cyclopentene in column 44, the additional cyclic olefins and dienes being pushed up the column may result in a need for increased reflux rates to meet overhead specifications. The use of low temperature, low pressure separator 36 avoids this scenario.

Figure 4:
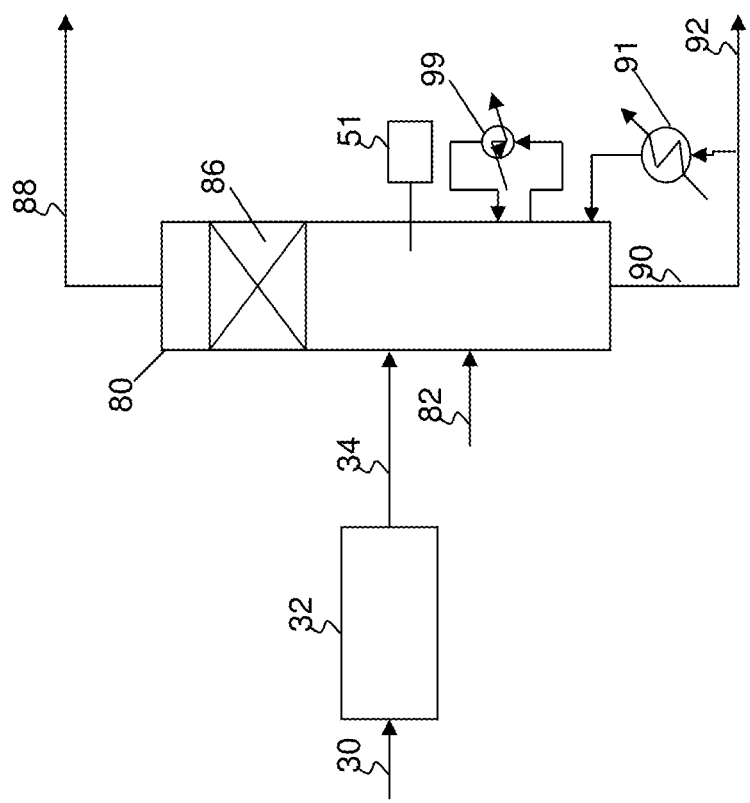

It has been found that dicyclopentadiene back cracking may also be avoided via limiting the reboiler temperature and residence time/holdup in the reboiler of column 44. For example, as illustrated in FIG. 4, the dimerization reactor 32 effluent 34 may be fed into a catalytic distillation reactor system 80, which may have one or more reaction zones 86. In column 80, the C5 olefin-containing feed is concurrently fractionated and selectively hydrogenated with hydrogen fed via flow line 82. The lighter components in the C5 olefin-containing feed traverse up the column, where any acetylenes and dienes may be reacted with hydrogen to produce additional olefins and paraffins, before being recovered as an overheads fraction 88. The heavier components in the C5 olefin-containing feed, including the dicyclopentadiene and C6+ components in the feed, traverse down the column and are recovered as a bottoms fraction 90.

A portion of bottoms fraction 90 may be reboiled and fed back to the column, such as via reboiler 91. The remaining portion of the bottoms fraction may be recovered as a bottoms product 92. As described for FIGS. 1-3, a feed preheater may be used to increase boilup of dienes into catalyst zone 86; one benefit of the feed preheater noted above was decreased reboiler duty. Additionally or as an alternative, the column may include an intermediate reboiler 99. A side draw may be withdrawn from column 80 below the feed location for hydrogen 82 and feed 34, and above main reboiler 91. The side draw may be at least partially vaporized in intermediate reboiler 99, and returned to column 80. The number of intermediate reboilers and temperatures of same should be sufficient to provide the desired vapor traffic in the column while limiting the temperature of the intermediate and main reboilers, such as to a temperature of less than about 300° F., and also reducing or minimizing the liquid holdup in the main reboiler. In this manner, the desired column traffic may be maintained while limiting the amount of back cracking occurring in the main reboiler.

As a drawback, activity of the hydrogenation catalyst is typically reduced as column temperature is reduced. The intermediate reboilers may provide a means to maintain catalyst activity while limiting the back cracking of dicyclopentadiene. Additionally, such a configuration may provide for reduced capital and operating requirements, eliminating one or more pieces of equipment, including the low temperature, low pressure separator. The total reboiler duty (intermediate plus main) has also been found to be roughly the same to meet cyclopentene specifications in the overhead product.

Catalysts useful in the hydrogenation reaction zone(s) may include Group 8 metals, such as cobalt, nickel, palladium, or platinum, alone or in combination, and/or Group 1B metals, such as copper, and/or other metals, such as a Group 5A or Group 6A metals, such as molybdenum or tungsten, on a suitable support, such as alumina, silica, titania, silica-alumina, titania-alumina, titania-zirconia, or the like. Normally the catalytic metals are provided as the oxides of the metals supported on extrudates or spheres. The metals may be reduced to the hydride form or other active states, if necessary, prior to use by exposure to hydrogen, for example.

The particular catalyst(s) and operating conditions in the hydrogenation reaction zone(s) may depend upon the particular C5-olefing containing feed(s) used, the overall flow scheme (i.e., use of or lack of guard beds, etc.), the desired conversion and selectivity, and the tolerance in end products for any isomerization that may occur under hydrogenation conditions, among other variables. Typical hydrogenation reaction zone operating conditions include temperatures in the range from 30° C. to 500° C. and pressures ranging from 1 to 100 bar.

Objectives of the overall system may include conversion of dienes to olefins, reducing the diene content to less than 500 ppmw, such as less than 200 ppmw, for example, as well as to minimize the loss of unsaturates, i.e., conversion of olefins to paraffins. When combined with a downstream metathesis process, linear olefin recovery may be considered more important than iso-olefin recovery because, in a downstream methathesis unit, one mole linear C5 olefin can theoretically produce three moles of propylene, while one mole of branched C5 olefin can produce one mole of propylene.

In addition to control of catalytic distillation reactor system operating parameters, it has been found that the catalyst used in each respective reaction zone may have an impact on overall system performance in meeting the objectives of reducing diene content and maximizing olefin recovery. In particular, it has been found that a catalyst system using a combination of palladium and nickel catalysts may provide sufficient activity and selectivity to meet the objective of reducing diene content at a very high olefin recovery.

In some embodiments, the catalyst system is divided into three reaction zones. A first reaction zone, located below the mixed C5 hydrocarbon feed point, contains a nickel-based catalyst. A second reaction zone, located above the mixed C5 hydrocarbon feed point, also contains a nickel-based catalyst. A third reaction zone is disposed above the second reaction zone and contains a palladium-based catalyst.

In addition to meeting the above objectives, the palladium and nickel catalyst systems described herein have been found to be extremely robust, maintaining activity and selectivity over extended run lengths. As would be appreciated by one skilled in the art, the expense and downtime associated with replacing catalysts in a catalytic distillation reactor system are different than those for fixed bed reactors, and thus the robustness of the catalyst systems herein is a significant benefit.

Figure 5:
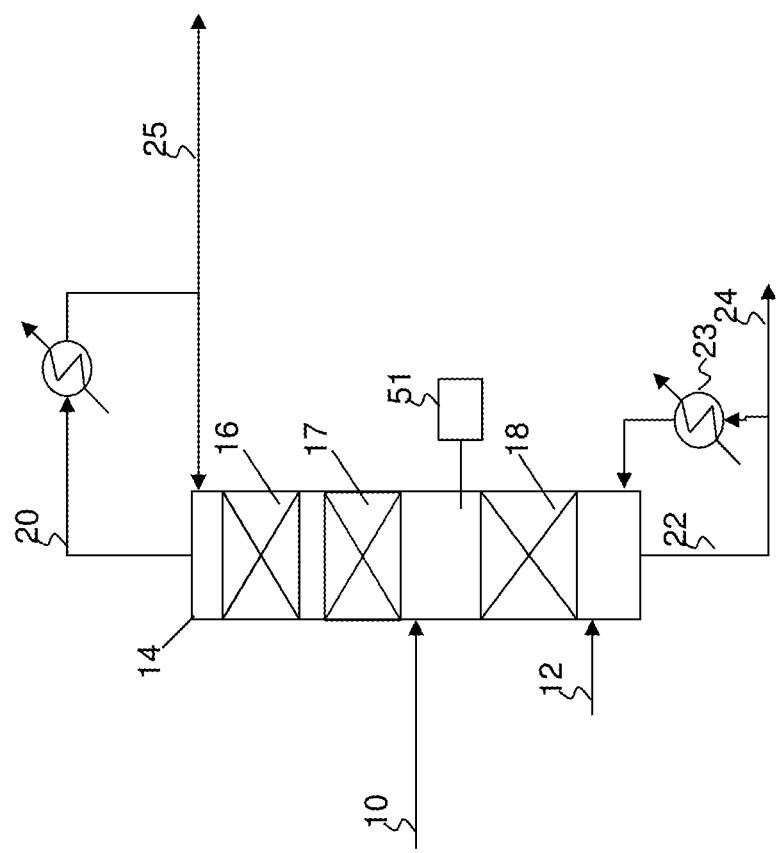

Referring now to FIG. 5, a catalytic distillation reactor system for producing C5 olefins and including a catalyst system according to embodiments herein is illustrated. A C5-olefin containing stream 10, such as described above and containing linear pentenes, dienes, acetylenes, cyclopentane, and cyclopentene, and a hydrogen stream 12 may be fed to a catalytic distillation reactor system 14.

Catalytic distillation reactor system 14 may include two or more reaction zones above the C5 feed elevation, and/or one or more reaction zones below the C5 feed elevation. The reaction zones disposed below the feed elevation contain a nickel-based catalyst. One or more lowermost reaction zones disposed above the feed elevation also contain a nickel-based catalyst. One or more uppermost reaction zones disposed above the feed elevation contain a palladium-based catalyst.

As illustrated, catalytic distillation reactor system 14 includes two reaction zones 16, 17 disposed above the C5 feed elevation and one reaction zone 18 disposed below the C5 feed elevation. Reaction zones 17 and 18 contain a nickel based catalyst, and Reaction zone 16 contains a palladium based catalyst. Hydrogen 12 may be introduced to the column below the lowermost reaction zone, zone 18, or may be split fed below two or more of the reaction zones.

In catalytic distillation reactor system 14, acetylenes and dienes in the C5 feed are selectively hydrogenated over the nickel-based and palladium-based hydrogenation catalyst, converting the acetylenes and dienes to olefins. Concurrent with the selective hydrogenation, the C5 feed is fractionated into an overheads fraction 20, including the olefins, and a bottoms fraction 22, including heavier or higher boiling feed components, such as unreacted dienes as well as cyclopentene and cyclopentane.

A portion of the bottoms fraction 22 may be vaporized in reboiler 23 and returned to column 14, and a remaining portion of the bottoms fraction 22 may be recovered as a bottoms product 24. The overhead fraction 20 may be condensed, a portion of the condensed overheads being returned to column 14 as a reflux, and a remaining portion being recovered as an overhead product fraction 25.

The nickel-based catalyst may include from about 1 wt % to about 40 wt % nickel, or from about 2 wt % to about 60 wt % nickel oxide, on a support. For example, useful nickel-based catalysts may have from about 3 wt % to about 40 wt % nickel, such as from about 5 wt %, 7.5 wt %, 10 wt % or 12.5 wt % to about 17.5 wt %, 20 wt %, 22.5 wt % or 25 wt % nickel, where any lower limit may be combined with any upper limit. The nickel may be disposed on any suitable support, such as silica, titania, alumina, clays, or diatomaceous earth, among others. The catalysts, in some embodiments, may be formed as an extrudate, such as in the form of pellets or spheres having a nominal size in the range from about 0.25 to about 5 mm, such as from about 0.5 to about 2.5 mm. The nickel-based catalysts may have a BET surface area in the range from about 20 to about 400 $m^2/g$, such as from about 40 to about 300 m²/g in some embodiments and from about 60 to about 240 m²/g in yet other embodiments, and may have a pore volume in the range from about 0.1 to about 0.8 ml/g, such as from about 0.2 μg to about 0.7 ml/g in some embodiments, and from about 0.25 to about 0.65 ml/g in yet other embodiments.

The palladium-based catalyst may include from about 0.1 wt % to about 3 wt % palladium, and the catalyst may be supplied in oxide form. For example, useful palladium-based catalysts may have from about 0.1 wt % to about 2.5 wt % palladium, such as from about 0.15 wt %, 0.2 wt %, 0.25 wt % or 0.3 wt % to about 0.6 wt %, 0.7 wt %, 0.8 wt % or 1.0 wt % palladium, where any lower limit may be combined with any upper limit. The palladium may be disposed on any suitable support, such as silica, titania, alumina, clays, or diatomaceous earth, among others. The catalysts, in some embodiments, may be formed as an extrudate, such as in the form of pellets or spheres having a nominal size in the range from about 0.25 to about 5 mm, such as from about 1.0 to about 4.0 mm. The palladium-based catalysts may have a BET surface area in the range from about 20 to about 600 m²/g, and may have a pore volume in the range from about 0.1 to about 1.0 ml/g, in various embodiments.

The above-described catalyst systems, including nickel-based and palladium-based catalysts, have been found useful in achieving a high diene conversion rate and a high olefin recovery rate. For example, diene conversion rates may be greater than 98 wt % in some embodiments; greater than 99 wt % in other embodiments, and greater than 99.5 wt % in yet other embodiments. Linear unsaturated recovery, defined as moles linear C5 olefins in the overhead distillate divided by moles linear C5 olefins and dienes in the mixed hydrocarbon stream, may be greater than 90% in some embodiments; greater than 92.5 wt % in other embodiments; greater than 95 wt % in other embodiments; and greater than 97.5 wt % in yet other embodiments. Branched unsaturated recoveries of greater than 90%, 91% or 92% are also possible.

Many of the references noted above indicate that nickel-based catalysts have poor selectivity as well as short catalyst life. However, in addition to the high selectivity noted above, the above-described catalyst system useful in embodiments herein have been found to be very stable, with experiments performed having exhibited no significant losses to activity or selectivity during over more than a year of operations. Overall, the unique combination and configuration of the catalytic distillation reactor systems and the catalyst systems described herein used therein may provide superior C5 olefin selectivity and catalyst stability.

With regard to the nickel-based catalysts, many of the references noted above suggest that a sulfiding step is required to achieve the desired activity and selectivity. In contrast, it has been found that a sulfiding step is not necessary, and processes according to embodiments herein may be performed without sulfiding the nickel-based catalysts while achieving very high diene conversion and olefin recovery rates.

In some embodiments, hydrogenation reaction zone temperatures may be within the range from about 30° C. to about 300° C. In other embodiments, hydrogenation reaction zone temperatures may be within the range from about 40° C. to about 250° C.; from about 50° C. to about 200° C. in other embodiments; and in the range from about 75° C. to about 175° C. in yet other embodiments. In embodiments where an upper and lower reaction zone are provided, the temperature in the lower bed will be greater than that of the upper bed, both of which are generally captured by the above ranges. Overheads and bottoms temperatures of the column may be greater than or less than the temperatures indicated above, the bottoms operating at a temperature proximate the boiling range of the heavier feed components at column pressure, and the overheads operating at a temperature proximate the boiling range of the lighter feed components and reaction products at column pressure.

Following selective hydrogenation of the acetylenic and diene compounds and separation of the linear and branched pentenes from cyclopentene, the resulting C5 olefin-containing product may be fed to a metathesis reactor for the production of propylene. For example, the linear pentenes may be reacted with ethylene in the presence of a metathesis catalyst or a combined metathesis/isomerization catalyst to produce propylene. When linear pentenes are fed to a conventional metathesis reactor, the following reactions may occur:

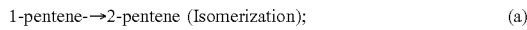

1-pentene-→2-pentene (Isomerization); (a)

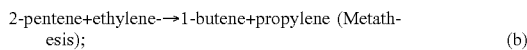

2-pentene+ethylene-→1-butene+propylene (Metathesis); (b)

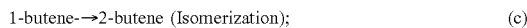

1-butene-→2-butene (Isomerization); (c)

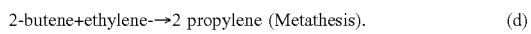

2-butene+ethylene-→2 propylene (Metathesis). (d)

1-Pentene is isomerized to 2-pentene. The metathesis reaction of 1-pentene with ethylene is non-productive (products are same as reactants). The overall linear C5 olefin reaction can thus be shown as:

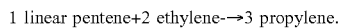

1 linear pentene+2 ethylene-→3 propylene.

Thus, the primary olefin of interest where metathesis is performed downstream is the linear pentenes. Branched pentenes provide 1 mole of propylene per mole.

The metathesis reaction products, including unreacted ethylene, propylene, butenes, and unreacted pentenes may then be recovered and forwarded to a separation zone, which may include one or more distillation columns and/or extractive distillation columns for separating the metathesis reactor effluent into various desired fractions, which may include an ethylene fraction, a propylene fraction, a butene and/or pentene fraction, and a heavies fraction. The ethylene fraction and butene/pentene fraction(s) may be recycled to the metathesis reaction zone for continued production of propylene.

Catalysts useful in the metathesis reactor may include any known metathesis catalyst, including oxides of Group VIA and Group VIIA metals on supports. Catalyst supports can be of any type and could include alumina, silica, mixtures thereof, zirconia, and zeolites. In addition to the metathesis catalyst, the catalyst contained in the metathesis reactor may include a double bond isomerization catalyst such as magnesium oxide or calcium oxide, for converting 1-butene and 1-pentene to 2-butene and 2-pentene, allowing for increased production of propylene via metathesis with ethylene. In some embodiments, the catalyst may include a promoter to reduce acidity; for example, an alkali metal (sodium, potassium or lithium), cesium, a rare earth, etc. In some embodiments, the metathesis or mixed metathesis/double bond isomerization catalyst may include those described in US20110021858 or US20100056839, for example.

The metathesis reactor may operate at a pressure between 1 and 40 bar in some embodiments, and between 5 and 15 bar in other embodiments. The metathesis reactor may be operated such that the reaction temperature is within the range from about 50° C. to about 600° C.; within the range from about 200° C. to about 450° C. in other embodiments; and from about 250° C. to about 400° C. in yet other embodiments. The metathesis reaction may be performed at a weight hourly space velocity (WHSV) in the range from about 3 to about 200 in some embodiments, and from about 6 to about 40 in other embodiments. The reaction may be carried out in the liquid phase or the gas phase, depending on structure and molecular weight of the olefin(s), by contacting the olefin(s) with the metathesis catalyst. If the reaction is carried out in the liquid phase, solvents or diluents for the reaction can be used, such as aliphatic saturated hydrocarbons, e.g., pentanes, hexanes, cyclohexanes, dodecanes, and aromatic hydrocarbons such as benzene and toluene are suitable. If the reaction is carried out in the gaseous phase, diluents such as saturated aliphatic hydrocarbons, for example, methane, ethane, and/or substantially inert gases, such as nitrogen and argon, may be present. For high product yield, the reaction may be conducted in the absence of significant amounts of deactivating materials such as water and oxygen.

EXAMPLES 1-3

Simulations were conducted to compare the performance of systems for selectively hydrogenating a C5 feed stream according to various embodiments herein. Simulations were carried out in ASPEN PLUS 7.2 (Aspen Technology, Inc., Burlington, Mass.).

EXAMPLE 1

In this Example, a process similar to that as illustrated in FIG. 1 is simulated. In the simulations, dienes and acetylenes are assumed to be selectively hydrogenated into olefins in the catalytic distillation reactor system, and all olefins are assumed to be saturated into alkanes in the total hydrogenation unit. Process conditions were as follows:

TABLE 2

Process Conditions for Example 1

| Example # | 1 |
|---|---|
| Heat soaker (32) | |
| Pressure, psia | 150 |
| Temperature, ° F. | 230 |
| CPD conversion | 94% |
| Low P/T column (36) | |
| Pressure, psia | 29.7 |
| Column stages | 30 |
| Condenser temp, ° F. | 136.7 |
| Reboiler temp, ° F. | 246.6 |
| Feed stage | 14 |
| Thiophene in distillate, ppm | 0 |
| Benzene in distillate, wt % | 0.5 wt % |
| C5 olefin recovery, % | 100% |
| C5CDHYDRO column (44) | |
| Column stages | 102 |
| C5 feed stage | 42 |
| H2 feed stage | 60 |
| Reaction zone stages | 30-40 |
| | 43-50 |
| Cyclopentene in OVHD, wt % | 0.5% |
| Linear olefin recovery, % | 84.79% |
| Total olefin recovery, % | 82.07% |
| Pressure, psia | 135 |
| Mass reflux ratio | 11.94 |
| Reboiler duty, btu/hr | 1.37e+7 |
| Bottom vs. feed molar ratio | 0.555 |
| PPH2, psi | 15.2 |
| Total Hydrogenation Unit (58) | |
| Pressure, psia | 260 |
| Temperature, ° F. | 230 |
| PPH2, psi | 181 |
| Recycle vs. feed molar ratio | 1.23 |

The simulated mass balance for Example 1 is shown in Table 3.

TABLE 3

| Mass Flow lb/hr | Stream | | | | | | | | |
|---|---|---|---|---|---|---|---|---|---|
| | 30 | 34 | 38 | 40 | 54 | 60 | 48 | 52 | Vent Loss |
| C4s | 46.29 | 46.29 | 46.29 | 0.00 | 0.00 | 0.00 | 26.70 | 0.00 | 19.58 |
| N-PENTANE | 576.77 | 576.77 | 576.76 | 0.01 | 31.95 | 187.93 | 660.40 | 7.50 | 64.85 |
| 2-METHYL-BUTANE | 641.04 | 641.04 | 641.04 | 0.00 | 0.00 | 229.21 | 754.06 | 0.00 | 116.19 |
| CYCLO PENTANE | 89.64 | 89.64 | 83.74 | 5.91 | 4021.15 | 4881.17 | 0.55 | 943.23 | 0.03 |
| CYCLO PENTENE | 651.19 | 651.19 | 645.16 | 6.02 | 835.30 | 0.00 | 26.02 | 195.94 | 1.93 |
| CYCLO PENTADIENE | 6718.23 | 403.09 | 401.76 | 1.33 | 0.00 | 0.00 | 0.00 | 0.00 | 0.00 |
| DICYCLO PENTADIENE | 0.00 | 5844.86 | 0.00 | 5844.86 | 0.00 | 0.00 | 0.00 | 0.00 | 0.00 |
| 1-PENTENE | 719.41 | 719.41 | 719.40 | 0.01 | 0.02 | 0.00 | 633.63 | 0.00 | 85.75 |
| CIS-2-PENTENE | 118.40 | 118.40 | 118.38 | 0.02 | 76.62 | 0.00 | 573.88 | 17.97 | 53.88 |
| TRANS-2-PENTENE | 193.38 | 193.38 | 193.35 | 0.03 | 74.98 | 0.00 | 1306.09 | 17.59 | 125.32 |
| 2-METHYL-1-BUTENE | 448.22 | 448.22 | 448.21 | 0.01 | 0.04 | 0.00 | 396.34 | 0.01 | 51.82 |
| 2-METHYL-2-BUTENE | 0.00 | 0.00 | 0.00 | 0.00 | 222.76 | 0.00 | 1029.58 | 52.25 | 84.50 |
| 3-METHYL-1-BUTENE | 60.89 | 60.89 | 60.89 | 0.00 | 0.00 | 0.00 | 49.66 | 0.00 | 11.23 |
| 2-METHYL-1,3-BUTADIENE | 1834.04 | 1349.42 | 1349.16 | 0.26 | 0.00 | 0.00 | 0.00 | 0.00 | 0.00 |
| CIS-1,3-PENTADIENE | 591.99 | 591.99 | 586.62 | 5.37 | 0.00 | 0.00 | 0.00 | 0.00 | 0.00 |

TABLE 3-continued

| Mass Flow lb/hr | Stream | | | | | | | | |
|---|---|---|---|---|---|---|---|---|---|
| | 30 | 34 | 38 | 40 | 54 | 60 | 48 | 52 | Vent Loss |
| 1-TRANS-3-PENTADIENE | 940.42 | 940.42 | 935.61 | 4.81 | 0.00 | 0.00 | 0.00 | 0.00 | 0.00 |
| 1,4-PENTADIENE | 347.86 | 347.86 | 347.86 | 0.00 | 0.00 | 0.00 | 0.00 | 0.00 | 0.00 |
| 1,2-PENTADIENE | 9.02 | 9.02 | 8.91 | 0.11 | 0.00 | 0.00 | 0.00 | 0.00 | 0.00 |
| BENZENE | 19148.88 | 19148.88 | 39.51 | 19109.37 | 32.00 | 0.00 | 0.00 | 7.51 | 0.00 |
| C6+ | 22864.32 | 23819.21 | 697.91 | 23121.31 | 3168.05 | 3213.22 | 0.00 | 743.12 | 0.00 |
| HYDROGEN | 0.00 | 0.00 | 0.00 | 0.00 | 0.00 | 51.34 | 1.00 | 0.00 | 442.53 |
| Total flow | 55999.99 | 55999.99 | 7900.56 | 48099.43 | 8462.88 | 8562.88 | 5457.90 | 1985.12 | 1057.61 |

EXAMPLE 2

In this Example, a process similar to that as illustrated in FIGS. 2 and 3 is simulated (Example 2A=no feed preheater; Example 2B=with feed preheater; Example 2C=with cyclopentene removal column). In these simulations, dienes and acetylenes are assumed to be selectively hydrogenated into olefins in the catalytic distillation reactor system, and all olefins are assumed to be saturated into alkanes in the total hydrogenation unit. Process conditions were as follows:

TABLE 4

Simulation conditions for Examples 2A, 2B, and 2C

| Case# | 2A | 2B | 2C |
|---|---|---|---|
| Heat soaker (32) | | | |
| Pressure, psia | 150 | 150 | 150 |
| Temperature, ° F. | 230 | 230 | 230 |
| CPD conversion | 94% | 94% | 94% |
| Low P/T column (36) | | | |
| Pressure, psia | 29.7 | 29.7 | 29.7 |
| Column stages | 30 | 30 | 30 |
| Condenser temp, ° F. | 136.7 | 136.7 | 136.7 |
| Reboiler temp, ° F. | 246.6 | 246.6 | 246.6 |
| Feed stage | 14 | 14 | 14 |
| Thiophene in distillate, ppm | 0 | 0 | 0 |
| Benzene in distillate, wt % | 0.5 wt % | 0.5 wt % | 0.5 wt % |
| C5 olefin recovery, % | 100% | 100% | 100% |
| Feed Heater (41) | | | |
| Heat Duty, btu/h | 0 | 1.22e+6 (35% vapor fraction) | |

TABLE 4-continued

Simulation conditions for Examples 2A, 2B, and 2C

| Case# | 2A | 2B | 2C |
|---|---|---|---|
| C5CDHYDRO column (44) | | | |
| Column stages | 102 | 102 | 52 |
| C5 feed stage | 42 | 42 | 22 |
| H2 feed stage | 60 | 60 | 40 |
| Reaction zone | 30-40 | 30-40 | 10-20 |
| Cyclopentene in OVHD, wt % | 0.5% | 0.5% | 11.8% |
| Linear olefin recovery, % | 74.63% | 75.74% | 82.40% |
| Total olefin recovery, % | 81.02% | 81.09% | 84.15% |
| Pressure, psia | 135 | 135 | 135 |
| Mass reflux ratio | 17.72 | 14.16 | 6.08 |
| Reboiler duty, btu/hr | 2.32e+7 | 1.70e+7 | 7.21e+6 |
| Bottom vs. feed molar ratio | 0.569 | 0.570 | |
| PPH2, psi | 10.5 | 12.9 | 12.9 |
| Total Hydrogenation Unit (58) | | | |
| Pressure, psia | 260 | 260 | 260 |
| Temperature, ° F. | 230 | 230 | 230 |
| PPH2, psi | 181 | 181 | 179 |
| Recycle vs. feed molar ratio | 1.18 | 1.17 | 1.0 |
| Cyclopentene Removal Column (62) | | | |
| Column stages | | | 65 |
| Feed stage | | | 40 |
| Cyclopentene in OVHD, wt % | | | 0.5% |
| Reboiler duty, btu/hr | | | 1.48e+7 |
| Pressure, psia | | | 74.7 |

The simulated mass balance for Examples 2A, 2B, and 2C are shown in Tables 5, 6, and 7, respectively.

TABLE 5

Example 2A

| Mass Flow lb/hr | Stream | | | | | | | | |
|---|---|---|---|---|---|---|---|---|---|
| | 30 | 34 | 38 | 40 | 54 | 60 | 48 | 52 | Vent Loss |
| C4s | 46.29 | 46.29 | 46.29 | 0.00 | 0.00 | 0.00 | 26.64 | 0.00 | 19.65 |
| N-PENTANE | 576.77 | 576.77 | 576.76 | 0.01 | 0.14 | 428.65 | 914.79 | 0.03 | 90.46 |
| 2-METHYL-BUTANE | 641.04 | 641.04 | 641.04 | 0.00 | 0.00 | 1.31 | 556.10 | 0.00 | 86.25 |
| CYCLOPENTANE | 89.64 | 89.64 | 83.74 | 5.91 | 4021.80 | 4881.69 | 0.28 | 943.38 | 0.02 |
| CYCLOPENTENE | 651.19 | 651.19 | 645.16 | 6.02 | 831.41 | 0.00 | 26.14 | 195.02 | 1.95 |
| CYCLOPENTADIENE | 6718.23 | 403.09 | 401.76 | 1.33 | 3.65 | 0.00 | 0.00 | 0.86 | 0.00 |

TABLE 5-continued

Example 2A

| Mass Flow lb/hr | Stream | | | | | | | | |
|---|---|---|---|---|---|---|---|---|---|
| | 30 | 34 | 38 | 40 | 54 | 60 | 48 | 52 | Vent Loss |
| DICYCLO PENTADIENE | 0.00 | 5844.86 | 0.00 | 5844.86 | 0.00 | 0.00 | 0.00 | 0.00 | 0.00 |
| 1-PENTENE | 719.41 | 719.41 | 719.40 | 0.01 | 0.00 | 0.00 | 633.12 | 0.00 | 86.28 |
| CIS-2-PENTENE | 118.40 | 118.40 | 118.38 | 0.02 | 0.34 | 0.00 | 464.96 | 0.08 | 43.98 |
| TRANS-2-PENTENE | 193.38 | 193.38 | 193.35 | 0.03 | 0.29 | 0.00 | 1115.31 | 0.07 | 107.82 |
| 2-METHYL-1-BUTENE | 448.22 | 448.22 | 448.21 | 0.01 | 0.00 | 0.00 | 396.07 | 0.00 | 52.14 |
| 2-METHYL-2-BUTENE | 0.00 | 0.00 | 0.00 | 0.00 | 1.09 | 0.00 | 1281.56 | 0.25 | 105.95 |
| 3-METHYL-1-BUTENE | 60.89 | 60.89 | 60.89 | 0.00 | 0.00 | 0.00 | 49.60 | 0.00 | 11.29 |
| 2-METHYL-1,3-BUTADIENE | 1834.04 | 1349.42 | 1349.16 | 0.26 | 0.18 | 0.00 | 0.01 | 0.04 | 0.00 |
| CIS-1,3-PENTADIENE | 591.99 | 591.99 | 586.62 | 5.37 | 167.56 | 0.00 | 0.00 | 39.31 | 0.00 |
| 1-TRANS-3-PENTADIENE | 940.42 | 940.42 | 935.61 | 4.81 | 233.74 | 0.00 | 0.00 | 54.83 | 0.00 |
| 1,4-PENTADIENE | 347.86 | 347.86 | 347.86 | 0.00 | 0.00 | 0.00 | 0.02 | 0.00 | 0.00 |
| 1,2-PENTADIENE | 9.02 | 9.02 | 8.91 | 0.11 | 2.64 | 0.00 | 0.00 | 0.62 | 0.00 |
| BENZENE | 19148.88 | 19148.88 | 39.51 | 19109.37 | 32.00 | 0.00 | 0.00 | 7.51 | 0.00 |
| C6+ | 22864.32 | 23819.21 | 697.91 | 23121.31 | 3168.02 | 3213.22 | 0.00 | 743.12 | 0.00 |
| HYDROGEN | 0.00 | 0.00 | 0.00 | 0.00 | 0.00 | 38.01 | 1.00 | 0.00 | 444.12 |
| Total flow | 56000.0 | 56000.0 | 7900.6 | 48099.4 | 8462.9 | 8562.9 | 5465.6 | 1985.1 | 1049.9 |

TABLE 6

Example 2B

| Mass Flow lb/hr | Stream | | | | | | | | |
|---|---|---|---|---|---|---|---|---|---|
| | 30 | 34 | 38 | 40 | 54 | 60 | 48 | 52 | Vent Loss |
| C4s | 46.29 | 46.29 | 46.29 | 0.00 | 0.00 | 0.00 | 26.64 | 0.00 | 19.64 |
| N-PENTANE | 576.77 | 576.77 | 576.76 | 0.01 | 3.37 | 401.96 | 886.89 | 0.79 | 87.65 |
| 2-METHYL-BUTANE | 641.04 | 641.04 | 641.04 | 0.00 | 0.00 | 27.91 | 579.18 | 0.00 | 89.78 |
| CYCLO PENTANE | 89.64 | 89.64 | 83.74 | 5.91 | 4021.01 | 4880.92 | 0.47 | 943.20 | 0.03 |
| CYCLO PENTENE | 651.19 | 651.19 | 645.16 | 6.02 | 820.41 | 0.00 | 26.13 | 192.44 | 1.95 |
| CYCLO PENTADIENE | 6718.23 | 403.09 | 401.76 | 1.33 | 14.35 | 0.00 | 0.00 | 3.37 | 0.00 |
| DICYCLO PENTADIENE | 0.00 | 5844.86 | 0.00 | 5844.86 | 0.00 | 0.00 | 0.00 | 0.00 | 0.00 |
| 1-PENTENE | 719.41 | 719.41 | 719.40 | 0.01 | 0.00 | 0.00 | 633.16 | 0.00 | 86.24 |
| CIS-2-PENTENE | 118.40 | 118.40 | 118.38 | 0.02 | 6.46 | 0.00 | 480.61 | 1.51 | 45.43 |
| TRANS-2-PENTENE | 193.38 | 193.38 | 193.35 | 0.03 | 5.63 | 0.00 | 1132.54 | 1.32 | 109.42 |
| 2-METHYL-1-BUTENE | 448.22 | 448.22 | 448.21 | 0.01 | 0.00 | 0.00 | 396.09 | 0.00 | 52.12 |
| 2-METHYL-2-BUTENE | 0.00 | 0.00 | 0.00 | 0.00 | 24.40 | 0.00 | 1252.13 | 5.72 | 103.46 |
| 3-METHYL-1-BUTENE | 60.89 | 60.89 | 60.89 | 0.00 | 0.00 | 0.00 | 49.61 | 0.00 | 11.28 |
| 2-METHYL-1,3-BUTADIENE | 1834.04 | 1349.42 | 1349.16 | 0.26 | 2.66 | 0.00 | 0.00 | 0.62 | 0.00 |
| CIS-1,3-PENTADIENE | 591.99 | 591.99 | 586.62 | 5.37 | 148.17 | 0.00 | 0.00 | 34.76 | 0.00 |
| 1-TRANS-3-PENTADIENE | 940.42 | 940.42 | 935.61 | 4.81 | 214.08 | 0.00 | 0.00 | 50.22 | 0.00 |
| 1,4-PENTADIENE | 347.86 | 347.86 | 347.86 | 0.00 | 0.00 | 0.00 | 0.00 | 0.00 | 0.00 |
| 1,2-PENTADIENE | 9.02 | 9.02 | 8.91 | 0.11 | 2.32 | 0.00 | 0.00 | 0.54 | 0.00 |
| BENZENE | 19148.88 | 19148.88 | 39.51 | 19109.37 | 32.00 | 0.00 | 0.00 | 7.51 | 0.00 |

TABLE 6-continued

Example 2B

| Mass Flow lb/hr | Stream | | | | | | | | |
|---|---|---|---|---|---|---|---|---|---|
| | 30 | 34 | 38 | 40 | 54 | 60 | 48 | 52 | Vent Loss |
| C6+ | 22864.32 | 23819.21 | 697.91 | 23121.31 | 3168.03 | 3213.22 | 0.00 | 743.12 | 0.00 |
| HYDROGEN | 0.00 | 0.00 | 0.00 | 0.00 | 0.00 | 38.87 | 1.00 | 0.00 | 444.03 |
| Total flow | 56000.0 | 56000.0 | 7900.6 | 48099.4 | 8462.9 | 8562.9 | 5464.5 | 1985.1 | 1051.0 |

TABLE 7

Example 2C

| Mass Flow lb/hr | Stream | | | | | | | | |
|---|---|---|---|---|---|---|---|---|---|
| | 30 | 34 | 38 | 40 | 54 | 60 | 48 | 52 | 66 | 64 |
| C4s | 46.29 | 46.29 | 46.29 | 0.00 | 0.00 | 0.00 | 46.29 | 0.00 | 46.29 | 0.00 |
| N-PENTANE | 576.77 | 576.77 | 576.76 | 0.01 | 11.84 | 272.33 | 847.80 | 1.35 | 834.55 | 13.25 |
| 2-METHYL-BUTANE | 641.04 | 641.04 | 641.04 | 0.00 | 0.03 | 103.99 | 745.01 | 0.01 | 744.98 | 0.03 |
| CYCLOPENTANE | 89.64 | 89.64 | 83.74 | 5.91 | 4043.13 | 4901.37 | 936.25 | 4048.89 | 0.06 | 936.19 |
| CYCLOPENTENE | 651.19 | 651.19 | 645.16 | 6.03 | 825.41 | 0.00 | 832.29 | 216.81 | 31.40 | 800.89 |
| CYCLOPENTADIENE | 6718.23 | 403.09 | 401.76 | 1.33 | 7.93 | 0.00 | 0.00 | 9.77 | 0.00 | 0.00 |
| DICYCLOPENTADIENE | 0.00 | 5844.86 | 0.00 | 5844.86 | 0.00 | 0.00 | 0.00 | 0.00 | 0.00 | 0.00 |
| 1-PENTENE | 719.41 | 719.41 | 719.40 | 0.01 | 0.13 | 0.00 | 719.36 | 0.04 | 719.24 | 0.12 |
| CIS-2-PENTENE | 118.40 | 118.40 | 118.38 | 0.02 | 19.99 | 0.00 | 610.79 | 1.21 | 587.35 | 23.44 |
| TRANS-2-PENTENE | 193.38 | 193.38 | 193.35 | 0.03 | 26.40 | 0.00 | 1377.76 | 1.72 | 1346.94 | 30.82 |
| 2-METHYL-1-BUTENE | 448.22 | 448.22 | 448.21 | 0.01 | 0.15 | 0.00 | 448.17 | 0.05 | 448.03 | 0.14 |
| 2-METHYL-2-BUTENE | 0.00 | 0.00 | 0.00 | 0.00 | 97.30 | 0.00 | 1382.80 | 1.85 | 1264.67 | 118.12 |
| 3-METHYL-1-BUTENE | 60.89 | 60.89 | 60.89 | 0.00 | 0.00 | 0.00 | 60.89 | 0.00 | 60.89 | 0.00 |
| 2-METHYL-1,3-BUTADIENE | 1834.04 | 1349.42 | 1349.16 | 0.26 | 3.50 | 0.00 | 0.00 | 4.32 | 0.00 | 0.00 |
| CIS-1,3-PENTADIENE | 591.99 | 591.99 | 586.62 | 5.37 | 86.93 | 0.00 | 0.00 | 107.18 | 0.00 | 0.00 |
| 1-TRANS-3-PENTADIENE | 940.42 | 940.42 | 935.61 | 4.81 | 112.34 | 0.00 | 0.00 | 138.51 | 0.00 | 0.00 |
| 1,4-PENTADIENE | 347.86 | 347.86 | 347.86 | 0.00 | 0.05 | 0.00 | 0.00 | 0.06 | 0.00 | 0.00 |
| 1,2-PENTADIENE | 9.02 | 9.02 | 8.91 | 0.11 | 1.44 | 0.00 | 0.00 | 1.77 | 0.00 | 0.00 |
| BENZENE | 19148.88 | 19148.88 | 39.51 | 19109.37 | 32.05 | 0.00 | 0.00 | 39.51 | 0.00 | 0.00 |
| C6+ | 22864.32 | 23819.21 | 698.94 | 23120.28 | 3194.30 | 3239.57 | 11.55 | 3926.94 | 0.00 | 11.55 |
| HYDROGEN | 0.00 | 0.00 | 0.00 | 0.00 | 0.00 | 45.64 | 195.59 | 0.00 | 195.59 | 0.00 |
| Total flow | 55999.99 | 55999.99 | 7901.59 | 48098.41 | 8462.90 | 8562.90 | 8214.55 | 8500.00 | 6280.00 | 1934.56 |

Comparing Example 1 to Example 2A, it can be seen from Tables 2 and 4 that a much lower reflux ratio/reboiler duty is required when adding some catalysts below the feed point in Example 1. The required catalytic distillation reactor system reboiler duty is 2.32e+7 btu/hr for Example 2A, while the required reboiler duty is 1.37e+7 btu/hr for Example 1. Without being bound to any particular theory, this may be due to the fact that the linear C5 dienes (e.g., cis-1,3-pentadiene and 1-trans-3-pentadiene) are heavier than linear C5 olefins. Hence some portion of dienes will move down toward the reboiler and get purged out from the column bottom stream for Example 2A. In Example 2A, the loss of cis-1,3-pentadiene and 1-trans-3-pentadiene to the bottom stream is 206.87 lb/hr and 288.57 lb/hr respectively, while in Example 1, the loss of cis-1,3-pentadiene and 1-trans-3-pentadiene is 0 lb/hr (simulation assumed complete conversion), as shown in Tables 3 and 5.

Comparing Examples 2A and 2C with respect to use of a cyclopentene removal column, it can be seen from Table 2 that a much shorter column and lower reflux ratio/reboiler duty are required for the catalytic distillation reactor system. The required column reboiler duty is 2.32e+7 btu/hr for Example 2A, while the required reboiler duty is 7.21e+6 btu/hr for Example 2C. In Example 2A the loss of cis-1,3- pentadiene and 1-trans-3-pentadiene to the bottom stream is 206.87 lb/hr and 288.57 lb/hr respectively, while in Example 2C, the loss of cis-1,3-pentadiene and 1-trans-3-pentadiene is 107.18 lb/hr and 138.51 lb/hr (Please see Table 5 and Table 7).

Comparing Examples 2A and 2B with respect to use of a feed preheater, it can be seen from Example 2A that the process can be successfully used to treat the stream cracker C5 feed to meet the downstream metathesis unit. Advantageously, the present inventors have discovered that adding a small preheater into the feed stream (Example 2B) may result in a substantial reduction in the reflux ratio or reboiler duty of the catalytic distillation reactor system. The required column reboiler duty is 2.32e+7 btu/hr for Example 2A without a pre feed heater, while the required reboiler duty is 1.70e+7 btu/hr for Example 2B with a small pre feed heater (1.22e+6 btu/hr). Without being bound to any particular theory, this may be due to the fact that the linear C5 dienes (e.g., cis-1,3-pentadiene and 1-trans-3-pentadiene) are heavier than linear C5 olefins. Hence some portion of dienes will move down toward the reboiler and are contained in the bottoms stream. In Example 2A the loss of cis-1,3-pentadiene and 1-trans-3-pentadiene to the bottom stream is 206.87 lb/hr and 288.57 lb/hr respectively, while in Example 2B, the loss of cis-1,3-pentadiene and 1-trans-3-pentadiene is 182.93 lb/hr and 264.3 lb/hr respectively (Please see Table 5 and Table 6). By pre-vaporizing C5 diene feed, more C5 dienes will move up into the reaction zone and get hydrogenated into valuable linear C5 olefins. Therefore, at a similar linear C5 olefin recovery rate, the column reflux ratio/reboiler duty could be substantially reduced by adding a pre-heater to pre-vaporize the C5 diene feed.

EXAMPLE 3

Steam cracker C5 dienes selective hydrogenation over palladium catalyst (about 0.6 wt % palladium on an alumina support) and nickel-based catalyst (33.3 wt % nickel on a support) were studied in a pilot plant. The objective of the pilot plant experiments was to reduce dienes from very high levels down to a very low level while minimizing the loss of unsaturates. In particular linear olefin recovery was considered more important than iso-olefin recovery; in a downstream methathesis unit, one mole linear C5 olefin can theoretically produce three moles of propylene, while one mole of branched C5 olefin can produce one mole of propylene. A simplified flow diagram of the pilot plant configuration used is illustrated in FIGS. 6 and 7, similar to the overall embodiment of FIG. 1.

Figure 6:
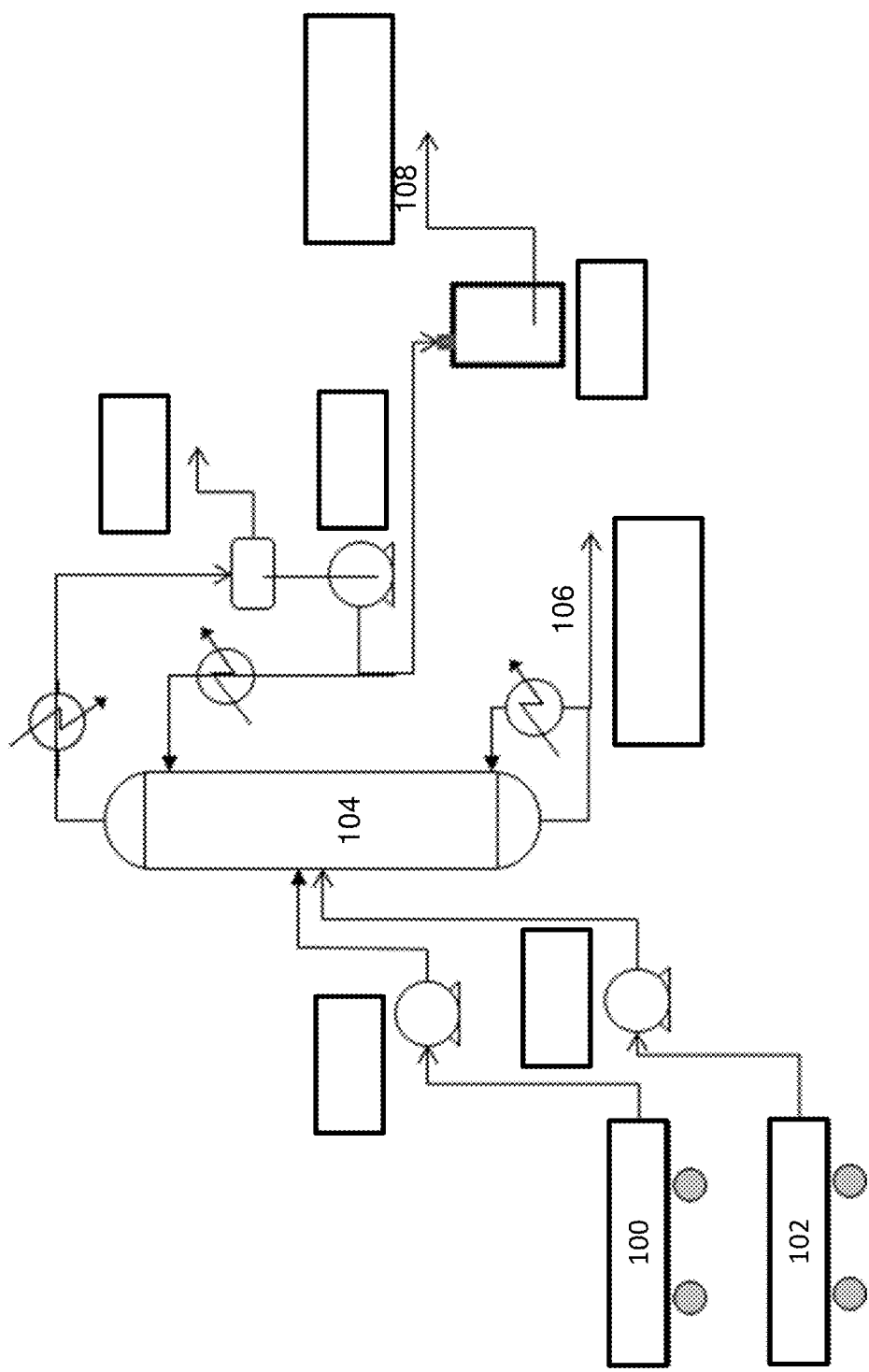
FIGS. 6-7 are simplified flow diagrams of pilot plant setups used to investigate processes and catalyst systems to produce C5 olefins according to embodiments disclosed herein.

Referring now to FIG. 6, C5 feed purification was performed by feeding a pygas 100 and a cyclopentane stream 102 to a distillation column 104. Column 104 was entirely filled with Raschig super rings. The aromatics and C6+ hydrocarbons were separated as bottom product 106 while the C5 hydrocarbons were recovered in the overhead stream 108. The overhead product stream was then used as a feed to the catalytic distillation reactor systems described below with respect to FIG. 7.

Figure 7:
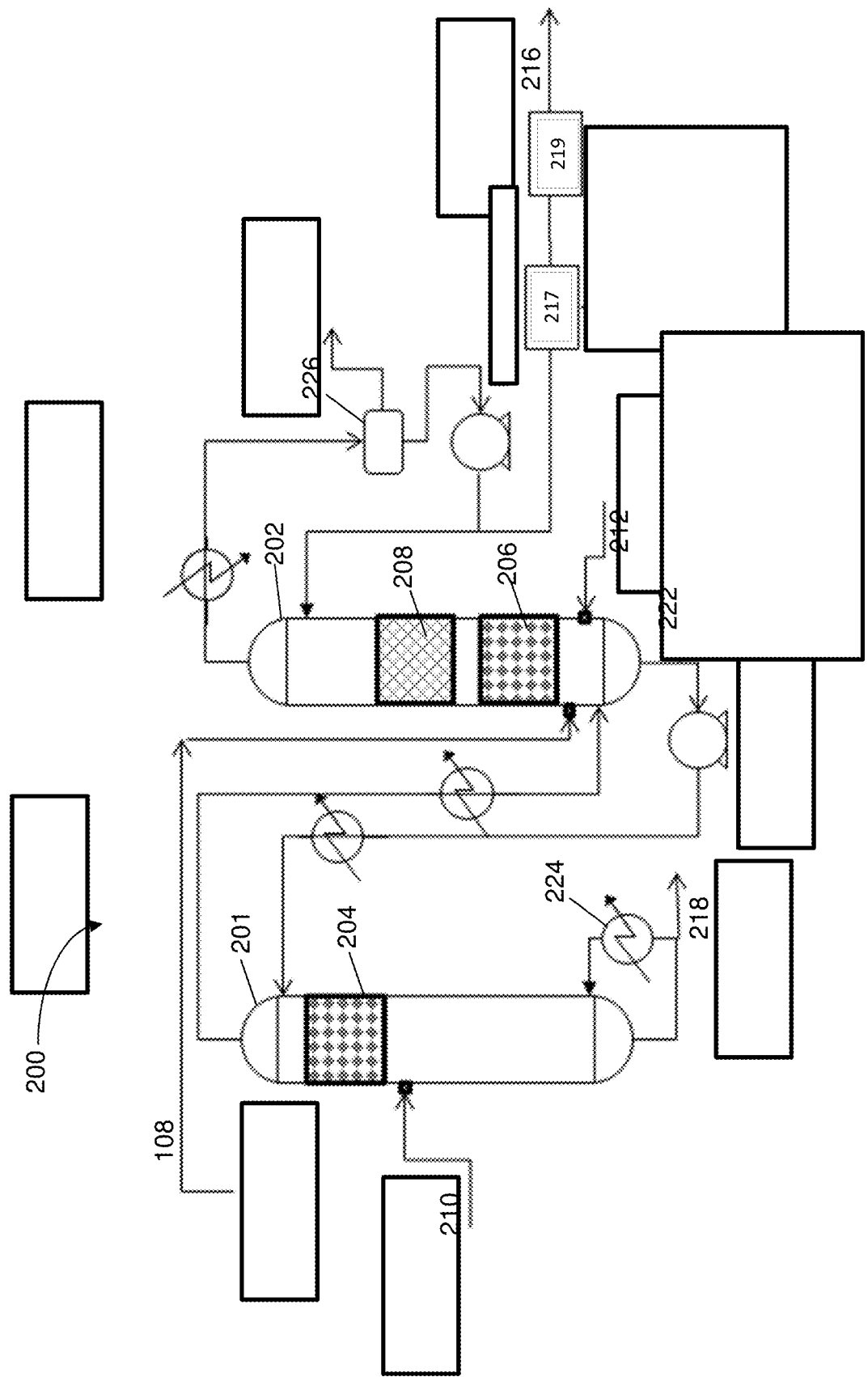

The catalytic distillation reactor systems 200 of FIG. 7, includes a distillation column reactor system 200 split into a stripping section 201 and a rectifying section 202. The stripping section 201 (below the elevation of feed 108 introduction) includes one reaction zone 204 containing a selective hydrogenation catalyst, and the rectifying section (above the elevation of feed 108 introduction) includes two reaction zones 206, 208 containing a selective hydrogenation catalyst. Reaction zones 204 and 206 contain the nickel-based catalyst, and reaction zone 208 contains the palladium-based catalyst. Hydrogen 210, 212 is introduced below reaction zones 204, 206, respectively. Dienes in feed 108 are converted within column 200 to olefins and recovered in the distillate product 216. The catalyst zones 206, 208 above the feed were used to convert light dienes such as isoprene and cyclopentadiene. Heavier linear dienes traverse down and were reacted in catalyst zone 204 to prevent significant yield loss to the bottoms product 218. Rectifying section 202 was charged with 8 ft of Raschig super rings at the top followed by 14 ft of palladium catalyst and 7 ft of nickel catalyst. Stripper section 201 was filled with 6 ft of Raschig super rings at the top followed by 7 ft of nickel catalyst and 18 ft of Raschig super rings.

Test conditions for and results from the pilot plant experiments are exemplified by the selection of data presented in Table 8-13 below.

TABLE 8

| Column 104 Conditions. | | | | |
|---|---|---|---|---|
| Condition/Sample Time | 1 | 2 | 3 | 4 |
| Pressure (psig) | 40 | 40 | 40 | 40 |
| Reboiler Temp (° F.) | 310.9 | 310.8 | 311.6 | 310.6 |
| Condenser Temp (° F.) | 83.9 | 85.4 | 88 | 83.8 |
| Mixed C5 Feed Rate (lb/h) | 60 | 60 | 60 | 60 |
| Cyclopentane Feed Rate (lb/h) | 10 | 10 | 10 | 10 |
| Overhead Draw Rate (lb/h) | 17.9 | 18 | 18 | 18 |

TABLE 9

| Column 200 Conditions. | | | | |
|---|---|---|---|---|
| Condition/Sample Time | 1 | 2 | 3 | 4 |
| Pressure (psig) | 70 | 70 | 70 | 70 |
| Reboiler Temp (° F.) | 246.5 | 246.3 | 246 | 246.4 |
| Condenser Temp (° F.) | 212.9 | 212.6 | 212.1 | 212.4 |
| Mixed C5 Feed Rate (lb/h) | 17.9 | 18 | 18 | 18 |
| Overhead Draw Rate (lb/h) | 7 | 7.07 | 7.06 | 6.96 |
| H2 Feed to column 201 (scfh) | 35.17 | 35.16 | 35.16 | 35.16 |
| H2 Feed to column 202 (scfh) | 5.09 | 5.09 | 5.09 | 5.09 |

TABLE 10

| Column 200 Feed Composition | | | | |
|---|---|---|---|---|
| Condition/Sample Time | 1 | 2 | 3 | 4 |
| n-pentane | 3.865 | 3.787 | 3.787 | 3.787 |
| Isopentane | 3.067 | 3.002 | 3.002 | 3.002 |
| Cyclopentane | 50.877 | 50.463 | 50.463 | 50.463 |
| Cyclopentene | 3.769 | 3.763 | 3.763 | 3.763 |
| Cyclopentadiene | 3.62 | 3.621 | 3.621 | 3.621 |
| Dicyclopentadiene | 0.092 | 0.086 | 0.086 | 0.086 |
| 1-pentene | 4.05 | 4.063 | 4.063 | 4.063 |
| Cis-2-pentene | 0.719 | 0.723 | 0.723 | 0.723 |
| Trans-2-pentene | 1.051 | 1.055 | 1.055 | 1.055 |
| 2-methyl-1-butene | 2.145 | 2.157 | 2.157 | 2.157 |
| 2-methyl-2-butene | 0.886 | 0.888 | 0.888 | 0.888 |
| 3-methyl-1-butene | 0.333 | 0.332 | 0.332 | 0.332 |
| 2-methyl-1,3-butadiene | 9.635 | 9.671 | 9.671 | 9.671 |
| Cis-1,3-pentadiene | 1.654 | 2.228 | 2.228 | 2.228 |
| Trans-1,3-pentadiene | 5.578 | 5.591 | 5.591 | 5.591 |
| 1,4-pentadiene | 2.159 | 2.167 | 2.167 | 2.167 |
| 1,2-pentadiene | 0.058 | 0.058 | 0.058 | 0.058 |
| 2,2-dimethylbutane | 2.035 | 2.018 | 2.018 | 2.018 |
| Other | 4.407 | 4.327 | 4.327 | 4.327 |

TABLE 11

Column 200 Overhead Draw Composition

| Condition/Sample Time | 1 | 2 | 3 | 4 |
|---|---|---|---|---|
| n-pentane | 10.289 | 10.06 | 10.370 | 10.601 |
| Isopentane | 7.034 | 7.021 | 7.121 | 7.244 |
| Cyclopentane | 1.092 | 1.463 | 1.095 | 0.929 |
| Cyclopentene | 7.220 | 7.362 | 6.670 | 6.035 |
| Cyclopentadiene | 0 | 0 | 0 | 0 |
| Dicyclopentadiene | 0 | 0 | 0 | 0 |
| 1-pentene | 4.689 | 4.668 | 4.527 | 4.482 |
| Cis-2-pentene | 7.692 | 7.705 | 7.790 | 7.838 |
| Trans-2-pentene | 26.986 | 26.957 | 27.374 | 27.594 |
| 2-methyl-1-butene | 9.043 | 8.929 | 8.983 | 9.051 |
| 2-methyl-2-butene | 20.227 | 20.048 | 20.438 | 20.633 |
| 3-methyl-1-butene | 2.005 | 2.034 | 1.903 | 1.845 |
| 2-methyl-1,3-butadiene | 0 | 0 | 0 | 0 |
| Cis-1,3-pentadiene | 0 | 0 | 0 | 0 |
| Trans-1,3-pentadiene | 0 | 0 | 0 | 0 |
| 1,4-pentadiene | 0.097 | 0.1 | 0.075 | 0.063 |
| 1,2-pentadiene | 0 | 0 | 0 | 0 |
| 2,2-dimethylbutane | 0 | 0 | 0 | 0 |
| Other | 3.626 | 3.653 | 3.654 | 3.685 |

TABLE 12

Column 200 Bottoms Draw Composition

| Condition/Sample Time | 1 | 2 | 3 | 4 |
|---|---|---|---|---|
| n-pentane | 0.008 | 0 | 0.017 | 0.020 |
| Isopentane | 0.001 | 0 | 0.007 | 0.010 |
| Cyclopentane | 90.882 | 90.804 | 90.363 | 90.013 |
| Cyclopentene | 4.652 | 4.515 | 4.432 | 4.590 |
| Cyclopentadiene | 0.035 | 0.029 | 0.030 | 0.033 |
| Dicyclopentadiene | 0.669 | 0.588 | 0.574 | 0.594 |
| 1-pentene | 0.002 | 0 | 0.002 | 0.002 |
| Cis-2-pentene | 0.004 | 0 | 0.005 | 0.006 |
| Trans-2-pentene | 0.012 | 0 | 0.013 | 0.014 |
| 2-methyl-1-butene | 0.001 | 0 | 0.001 | 0.001 |
| 2-methyl-2-butene | 0.016 | 0 | 0.018 | 0.020 |
| 3-methyl-1-butene | 0 | 0 | 0 | 0 |
| 2-methyl-1,3-butadiene | 0.006 | 0 | 0.006 | 0.006 |
| Cis-1,3-pentadiene | 0.002 | 0 | 0.002 | 0.002 |
| Trans-1,3-pentadiene | 0.009 | 0 | 0.009 | 0.008 |
| 1,4-pentadiene | 0 | 0 | 0 | 0 |
| 1,2-pentadiene | 0 | 0 | 0 | 0 |
| 2,2-dimethylbutane | 0.334 | 1.114 | 1.560 | 1.771 |
| Other | 3.367 | 2.95 | 2.961 | 2.910 |

TABLE 13

Experimental Results

| Condition/Sample Time | 1 | 2 | 3 | 4 |
|---|---|---|---|---|
| Linear diene Conversion (wt %) | 99.54 | 99.61 | 99.65 | 99.70 |
| Branched Diene Conversion (wt %) | 99.97 | 100 | 99.97 | 99.96 |
| Linear Unsaturated Recovery (wt %) | 99.12 | 95.70 | 96.39 | 95.44 |
| Branched Unsaturated Recovery (wt %) | 91.93 | 91.33 | 92.14 | 91.34 |

From the summary of results in Table 13, it can be concluded that the dual catalyst system according to embodiments herein may provide excellent catalyst performance, with high selectivity toward the desired olefin products. In addition, the catalyst system has been tested in pilot plant close to a year, without showing observable catalyst deactivations, the catalyst system thus being very stable and robust in the catalytic distillation reactor system. While the cyclopentene concentration in the overheads of the pilot plant system was relatively high, more distillation stages above the catalyst bed or an ensuing cyclopentene removal column may be used to reduce cyclopentene level to a desired level.

As described above, embodiments disclosed herein relate generally to processes and systems for the production of linear C5 olefins from C5 feeds, such as steam cracker C5 feeds and FCC C5 feeds. More particularly, embodiments disclosed herein relate to processes for producing C5 olefins via catalytic distillation reaction systems, the catalytic distillation reaction system including a bed of hydrogenation catalyst for converting C5 dienes to C5 olefins, among other reactions.

Control of the catalytic distillation reaction system is complex. In addition to the need to control overhead cyclopentene and diene concentrations, the process is complicated by several additional factors: the C5s are relatively close boiling; one or more of the reaction zones may require an amount of diluent or inert compounds to aid in heat removal; feed composition variations; weather changes; hydrogenation catalyst activity changes; and other various process disruptions and variables that may be encountered, affecting not only product purity, but energy usage and olefin recovery efficiency.

Typical process control for a distillation column may include temperature control. For example, for a typical temperature controller in a distillation tower, a temperature on a selected tray is controlled by adjusting distillation process variables, such as heat input to the column reboiler. However, it has been found very difficult to control and/or optimize a C5 selective hydrogenation column (a C5 catalytic distillation reaction system for selectively hydrogenating C5 dienes in a mixed C5 feed) using a typical temperature control scheme. Because of the relatively close boiling points of the C5 olefins, cyclopentene, and cyclopentane, the temperature profile along the catalytic distillation reactor system is relatively flat. Thus, minor changes in temperature can shift the concentration of various C5 components within the column. It has been found that these shifts may negatively impact the catalyst zones, and that the C5 olefin recovery can be quickly deteriorated.

It has been found that improved control of the catalytic distillation reactor system and increased olefin recovery may be achieved by controlling a concentration profile of a selected inert compound or compounds within the catalytic distillation reactor system. In some embodiments, the selected inert compound may be an added diluent, such as a C5, C6, or C7 hydrocarbon, a diluent or inert compound present in the C5 feedstock, or a diluent formed in situ, such as via hydrogenation of cyclopentene to form cyclopentane. The selected inert compound should have a boiling point greater than a boiling point of the target overhead product, such as 1-pentene or 2-pentene, and in some embodiments may have a boiling point or range intermediate that of the lowest and highest boiling compounds in the column feed. Additionally, the selected inert compound is preferably not a reactive component fed to the catalytic distillation reaction system, such as a pentadiene, a product of the selective hydrogenation, such as 1-pentene or 2-pentene, or a very minor component in the mixed hydrocarbon feedstock. The high or intermediate boiling point or range and concentration of the selected inert compound(s) may thus allow for a reliable presence at a measurable concentration at one or more elevations within the column. While a reactive or minority component may be used, such compounds are subject to column dynamics, and may not be a reliable source for control.

For example, it has been found that improved control of the catalytic distillation reactor system may be achieved by controlling a cyclopentane concentration profile within the catalytic distillation reactor system. Alternatively, improved control of the catalytic distillation reactor system may be achieved by controlling a combined cyclopentene and cyclopentane concentration profile within the catalytic distillation reactor system. In this manner, the cyclopentane and cyclopentene in the catalyst beds may be controlled to prevent the concentration of the inert compounds from becoming too low, thus reducing the C5 olefin recovery, or too high, thus contaminating the C5 olefin product with cyclopentene. Maintaining a proper concentration profile of cyclopentane and cyclopentene throughout the catalyst zones has been found effective at providing the desired column control, hydrogenation performance, separation, and olefin recovery. Maintaining an appropriate cyclopentane and/or cylcopentene concentration profile within the column may maximize C5 olefin recovery and C5 diene conversion while at the same time control the cyclopentene content in the C5 olefin overhead product stream.

The concentration profile may be controlled by measuring at least one of a composition and a density at one or more column elevations. The method for measuring composition or density may be selected based on robustness, reliability, cost, ease of implementation, and other factors related to the process and site. As used herein, "column elevation" refers to a sample or measurement point, such as a measurement taken on a vapor or liquid within the column, i.e, between the lowermost stage and uppermost stage of the column, including the overhead (stream 20 in FIG. 8 (described below), for example), but not including the overhead liquid draw (stream 25 in FIG. 8, for example).

In some embodiments, the concentration profile of a selected inert compound within the column may be measured and controlled by use of an on-line gas chromatograph (GC). For example, a PGC2000 E2 on-line gas chromatographs, available from ABB Inc., Wickliffe, Ohio, may be used to measure discrete hydrocarbons in a mixed hydrocarbon stream. The GC may analyze a sample from one or more column elevations, where the sample may be a gas phase sample or a liquid phase sample. For example, the GC may analyze a sample from one or more elevations to determine a concentration of cyclopentane and/or cyclopentene at the elevation or a concentration profile of cyclopentane and/or cyclopentene within the column. Column variables may then be adjusted to control the column elevation(s) at or near the target concentration. For example, in one embodiment, one or more sample analyzers may be cascaded with flow controllers to control one or more of overhead draw rate and reboiler heat input, among other variables.

In other embodiments, the concentration profile of a selected inert compound within the column may be controlled by measuring and controlling a liquid density at one or more column elevations. A density measurement device or density meter may be disposed in a downcomer or liquid re-distribution point within the column, where a direct measurement of density may be made. Alternatively, density may be indirectly measured via a density profiler, such as a gamma ray backscatter density profiler disposed adjacent the column to measure a density of fluids, such as in a downcomer, within the column. Frothing of the liquids in a downcomer or elsewhere within the column may disrupt direct measurement, whereas a density profiler may be able to directly accommodate varying froth levels; nonetheless, both systems may have their advantages and disadvantages. Column variables may then be adjusted to control the column elevation(s) at or near the target density. For example, in one embodiment, one or more density analyzers may be cascaded with flow controllers to control one or more of overhead draw rate and reboiler heat input, among other variables.

Density control indirectly controls the concentration profile of the target inert compound within the column. The specific gravity of pentane is about 0.64, 1,3-pentadiene 0.683, cyclopentane 0.751, and cyclopentene 0.771. Density may be related to composition (e.g., the density of the mixture is a function of the concentration or mass fraction of the various components in the mixture, temperature and pressure, oversimplified, for example, as $\rho_{mix}$=f([pentene], [cyclopentene], [pentadiene], [cyclopentane], T, P)). At column pressure and elevation temperature, the density of the mixture may thus be used to control a concentration of the inert diluent. Knowing the relationship between density and composition, one skilled in the art may thus be able to use density as an indirect means for composition control—as the composition becomes heavier, the concentration of cyclopentene and cyclopentane at the elevation is increasing, and as the composition becomes lighter, the concentration of cyclopentene and cyclopentane at the elevation is decreasing.

When measuring density, the control scheme may be based on density or composition. As noted above, density is an indicator of composition. In some embodiments, a density set point may be used as a control basis. In other embodiments, a concentration set point may be used as a control basis, where the composition is determined based on the measured density.

Inert or diluent compounds that may be selected as a control basis may have a boiling point or boiling range of greater than about 100° F., for example, so as to preferentially remain in the lower portions of the column and not be collected with the overhead fraction in any significant content, the target olefins, 1-pentene and 2-pentene having a normal boiling point lower than the inert or diluent compounds selected. In some embodiments, the inert or diluent compounds selected as a control may have a boiling range or boiling point in the range from about 100° F. to about 125° F., such as from about 102.5° F. to about 122.5° F. or from about 111° F. to about 121° F.

Inert or diluent compounds that may be selected as a control basis may have a specific gravity of greater than about 0.675, for example, so as to distinguish over the lower density target olefins and allow an operator or control system to determine a response to changes in measured density. In some embodiments, the inert or diluent compounds selected as a control may have a specific gravity in the range from about 0.675 to about 0.9, such as from about 0.7 to about 0.8 or from about 0.73 to about 0.78.

When controlling based upon diluent compound concentration, one or more column operating parameters may be adjusted to maintain a set point concentration. For example, a controller may be configured to perform one of the following actions: decrease an overhead flow and increase a reflux flow when a diluent compound concentration profile starts to move up the column and the reflux flow is below a column flooding value; increase an overhead flow and decrease reflux flow when a diluent compound concentration profile starts to move down the column and the reflux flow is above a minimum design value (e.g., where the reflux is enough to wet the catalyst, dissipate the reaction heat, and remove cyclopentene from the C5 olefins); decrease a reboiler duty (if the reflux flow needs to be maintained a constant value) and an overhead flow when the diluent compound concentration profile starts to move up the column; or, increase a reboiler duty (if the reflux flow needs to be maintained a constant value) and an overhead flow when the diluent compound concentration profile starts to move down the column.

When controlling based upon density, one or more column operating parameters may be adjusted to maintain a set point density. For example, a controller may be configured to perform one of the following actions: decrease an overhead flow and increase a reflux flow when a density profile indicates a concentration of a target compound is starting to move up the column and the reflux flow is below a column flooding value; increase an overhead flow and decrease a reflux flow when a density profile indicates a concentration of a target compound is starting to move down the column and the reflux flow is above a minimum design value (e.g., where the reflux is enough to wet the catalyst, dissipate the reaction heat, and remove cyclopentene from the C5 olefins); decrease a reboiler duty (if the reflux flow needs to be maintained a constant value) and an overhead flow when the density profile indicates a concentration of a target compound is starting to move up the column; or, increase a reboiler duty (if the reflux flow needs to be maintained a constant value) and an overhead flow when the density profile indicates a concentration of a target compound is starting to move down the column.

The above are one envisioned manner to meet the target objective of maintaining an appropriate concentration profile of the diluent compound within the column, which may aid in one or more of maximizing C5 olefin recovery, maximizing C5 diene conversion, and controlling cyclopentene in the C5 olefin product stream. Other control schemes, as well as adjustment of other process variables, may also be employed to meet the objectives of improved control and process efficiency.

Figure 8:
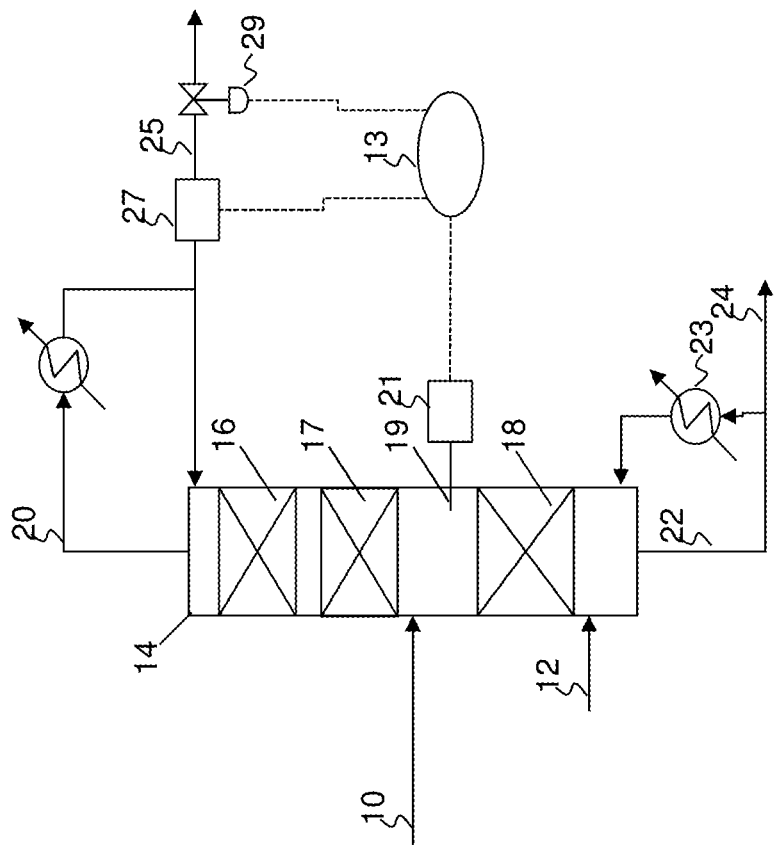

Referring now to FIG. 8, a simplified flow diagram of a process for producing C5 olefins from a mixed hydrocarbon stream according to embodiments herein is illustrated. A C5-olefin containing stream 10, such as described above and containing linear pentenes, dienes, acetylenes, cyclopentane, and cyclopentene, and a hydrogen stream 12 may be fed to a catalytic distillation reactor system 14. Catalytic distillation reactor system 14 may include one or more reaction zones above the C5 feed elevation, and/or one or more reaction zones below the C5 feed elevation. As illustrated, catalytic distillation reactor system 14 includes two reaction zones 16, 17 disposed above the C5 feed elevation and one reaction zone 18 disposed below the C5 feed elevation. Hydrogen 12 may be introduced to the column below the lowermost reaction zone, zone 18, or may be split fed below two or more of the reaction zones.

In catalytic distillation reactor system 14, acetylenes and dienes in the C5 feed are selectively hydrogenated over a hydrogenation catalyst, converting the acetylenes and dienes to olefins. Some olefins may also be converted to paraffins, but catalyst selectivity, hydrogen concentrations, and reaction zone temperatures may be maintained to limit olefin hydrogenation, selectively hydrogenating the more reactive dienes and acetylenes. Concurrent with the selective hydrogenation, the C5 feed is fractionated into an overheads fraction 20, including the olefins, and a bottoms fraction 22, including heavier or higher boiling feed components, such as unreacted dienes as well as cyclopentene and cyclopentane.

A portion of the bottoms fraction 22 may be vaporized in reboiler 23 and returned to column 14, and a remaining portion of the bottoms fraction 22 may be recovered as a bottoms product 24. The overhead fraction 20 may be condensed, a portion of the condensed overheads being returned to column 14 as a reflux, and a remaining portion being recovered as an overhead product fraction 25.

As noted above, it is desired to limit a content of dienes and cyclopentene in overhead product fraction 25. It is also desired to maintain stable column operations, even though the column may have a relatively flat temperature profile, while meeting the overhead specifications and maximizing C5 olefin recovery and C5 diene conversion. The column may include one or more sample points 19 for withdrawing and feeding a liquid sample or a vapor sample to an analyzer 21, such as a gas chromatograph (GC) for determining a concentration of cyclopentene and/or cyclopentane in the column at the sample point elevation.

As illustrated in FIG. 8, column 14 includes one sample point 19 disposed intermediate the upper reaction zone 17 and lower reaction zone 18, as well as below the C5 feed point elevation. Additional or alternative sample locations may be used, and may be fed to separate analyzers or a single analyzer capable of serial or parallel analyses.

The elevation of the sample point may be selected based on column dynamics estimated for a particular feedstock and reaction zone configuration. For example, it may be determined, via simulation or sampling for example, that a change in concentration of cyclopentane is approximately at a peak value within the column at a particular elevation. A sample point may be located proximate that elevation, such as within a few stages or equivalent heights of packing for example. As used herein, proximate an elevation refers to being within a few distillation stages, such as within about 5 or 10 stages for a column having 100 stages, for example, where stage or distillation stage refers to actual distillation trays or an equivalent (theoretical or otherwise) height of packing. Thus, where a desired sample point is determined to be approximately at stage 85, a sample point may be located between stages 80 and 90, for example. The actual sample elevation may depend upon several factors, including accessibility at the desired elevation. Preferably, the sample point is not located proximate an elevation where a change in concentration of the control compounds is small within the column, as this may hamper the ability of a control system to properly control the column, the concentration decreasing regardless of direction, making determination of the action to be taken difficult as it cannot readily be determined if the concentration profile is moving up or down the column.

The GC may then analyze the sample to determine a concentration of cyclopentene and/or cyclopentane at the sample elevation. The sampling result, such as a summation of the cyclopentane and cyclopentene concentrations, may then be provided to a controller 13, such as a digital control system or other types of control systems known in the art. Controller 13 may be a flow indicator controller (FIC) configured to control the overhead flow control loop, including flow meter 27 and flow control valve 29, to maintain a desired set point concentration of cyclopentane at the sample elevation. If the summation of cyclopentane and cyclopentene profile starts to move up the column, the overhead flow can be reduced (i.e., reflux flow may need to be increased) and allow more flow to the bottom stream, while if the cyclopentane and cyclopentene profile starts to move down the column, the overhead flow can be increased (i.e., reflux flow may need to be decreased) and at the same time reduce column bottom flow.

Figure 9:
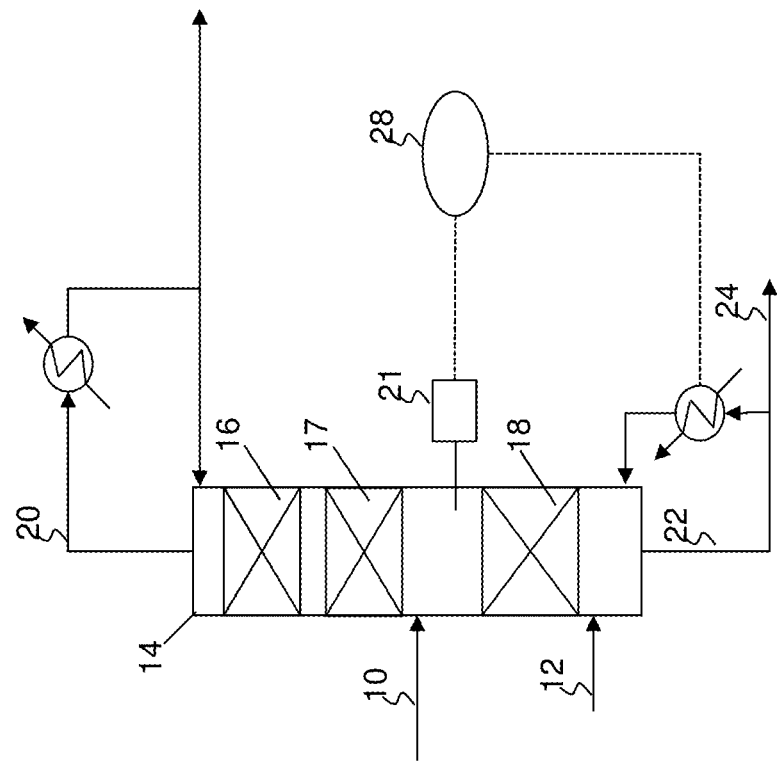
FIGS. 8-11 are simplified flow diagrams of processes to produce C5 olefins according to embodiments disclosed herein.

C5 diene hydrogenation is highly exothermic and enough reflux flow should be maintained to wet the catalyst and prevent reaction run away, and hence for some cases, such as for steam cracker C5 feeds having high concentrations of dienes, it may be more beneficial to keep a constant reflux flow to the column. In such an instance, it may be more beneficial to vary reboiler duty to either decrease or increase overhead flow if the cyclopentane and cyclopentene concentration profile starts to move up or down, such as illustrated in FIG. 9, rather than simply increase more overhead flow by reducing reflux flow. As illustrated in FIG. 9, where like numerals represent like parts, the sampling result, such as a summation of the cyclopentane and cyclopentene concentrations, may be provided to a controller 28. Controller 28 may be a heat indicator controller (HIC) configured to control heat input to the reboiler, such as by varying a flow, pressure, or temperature of a heat exchange fluid, such as steam or water, provided to the reboiler.

Figure 11:
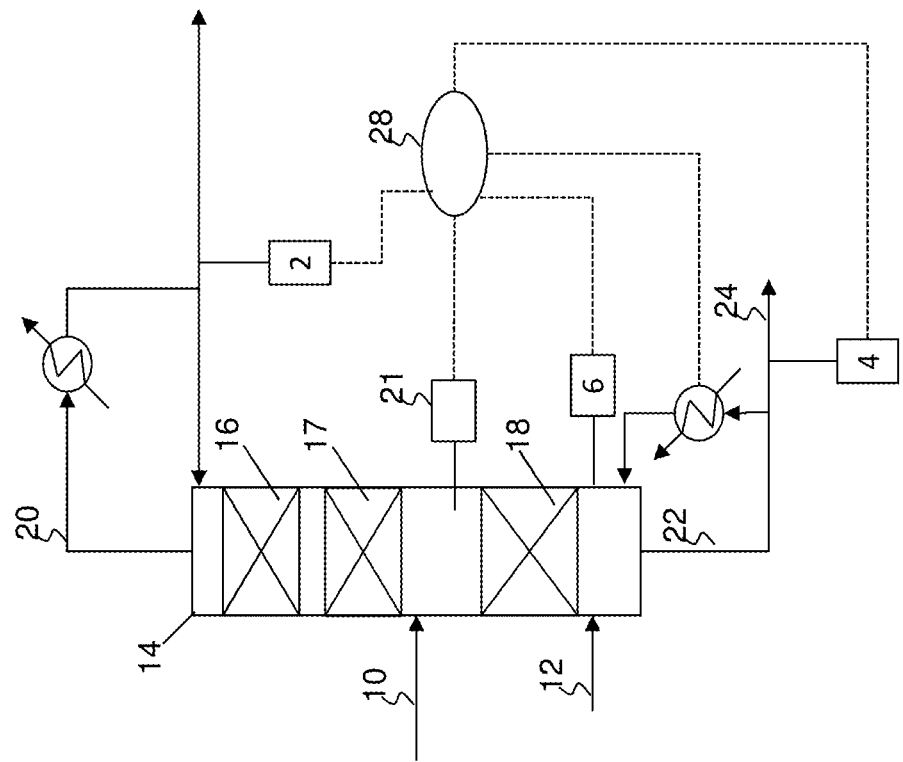
Figure 10:
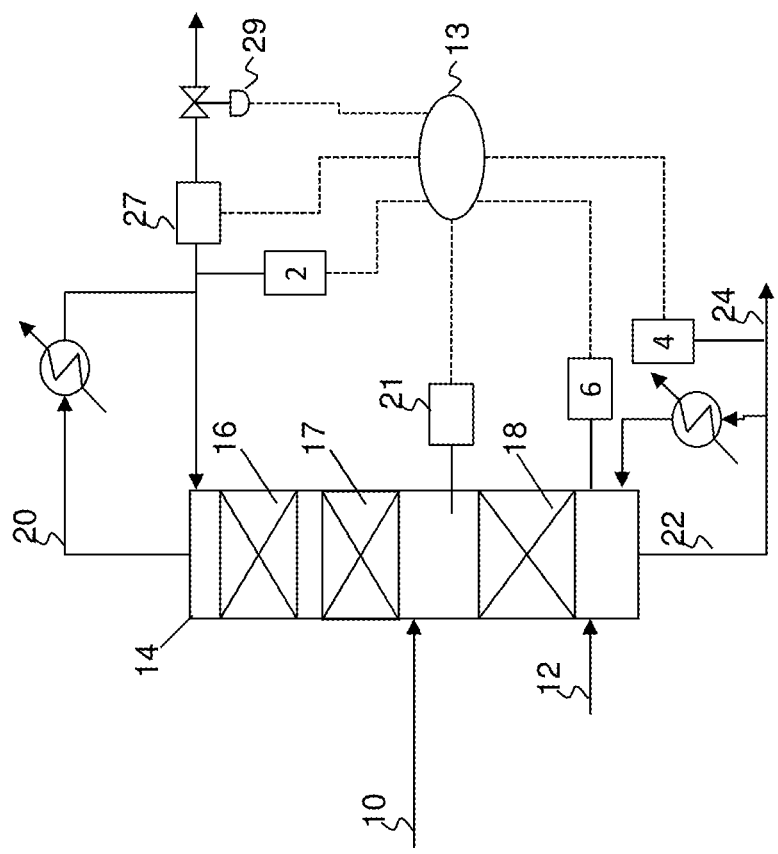

Embodiments disclosed herein may include systems having one or more sample points. FIGS. 8 and 9 include a single sample point at an elevation between the upper and lower catalyst beds and below the feed point. For very tall columns, such as where the rectification and stripping portions of the column may be split into two columns linked to operate as a single distillation column, a sample point may be disposed within or proximate the mid-reflux stream or mid-reboil stream. Additional sample points may be disposed at other locations along the column, including below, intermediate, or above reaction zone(s) located in the rectification and stripping portions of the column, in the overhead vapor draw, in the overhead product draw, in the bottoms liquid draw, and/or in the bottoms product draw. These additional sample points may be used to monitor performance of the column, and/or may be used to provide additional inputs to the control system. For example, as illustrated in FIGS. 10 and 11, where like numerals represent like parts, additional analyzers 2, 4, 6 may be used to determine the concentration of cyclopentene and/or cyclopentane in the overhead product draw 25, the bottoms product draw 24, and below the lower catalyst zone 18, respectively. Sample analysis results from one or more of analyzers 2, 4, 6 may be used to monitor system performance based on controlling of the system via the concentration profile determined via analyzer 21; alternatively or additionally, one or more of analyzers 2, 4, 6 may be used as an input to controller 13, 28 to enhance the control of the system and effect the desired concentration profile within the column. Such embodiments may further the enhancement in conversion of dienes and recovery of olefins via concentration profile control.

Figure 13:
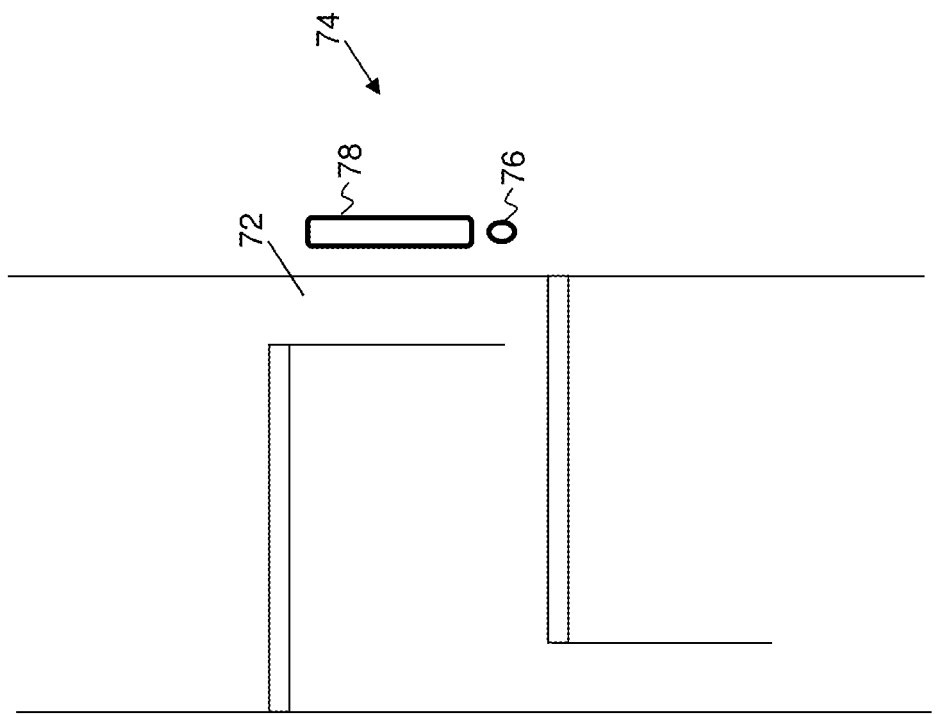
FIGS. 12 and 13 are schematic diagrams illustrating placement of density measurement devices for processes to produce C5 olefins according to embodiments disclosed herein.
Figure 12:
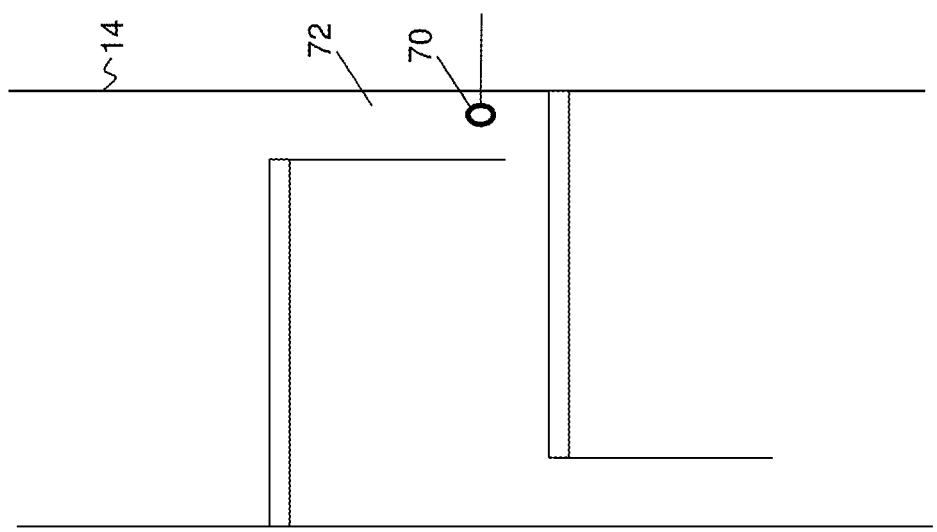

As described above with respect to FIGS. 8-11, analyzers, such as GCs, may be disposed and used for measurement of concentrations at various column elevations. One or more of analyzers 21, 2, 4, 6 may be a density analyzer or density measurement device. For example, as illustrated in FIG. 12, distillation column reactor system 14 may include one or more density measurement devices 70 disposed within a downcomer 72. For example, a density sensor, such as one using an oscillating U-tube principle, may be used. An output from the density measurement device may then be communicated to a controller 13, 28 (FIGS. 8-11) for control of the column based upon the density profile or a concentration profile determined based on the density profile. As another example, such as illustrated in FIG. 13, distillation column reactor system 14 may include one or more gamma ray backscatter density profilers 74 that may be used to measure a density of the fluids within a downcomer 72. For example, a density profiler such as described in US20130123990 (Thermo Fisher Scientific Inc., Sugarland, Tex.) may be used. Gamma rays emitted from source 76 and backscattered to detector 78 may be used to determine a density of the fluid in the downcomer. An output from the detector 78 may then be communicated to a controller 13, 28 (FIGS. 8-11) for control of the column based upon the density profile or a concentration profile determined based on the density profile.

Referring again to FIGS. 1-4, in catalytic distillation reactor system 44, the C5 olefin-containing feed is concurrently fractionated and selectively hydrogenated, where control of the catalytic distillation reactor system may include a control scheme as described above with respect to one or more of FIGS. 8-13 via an analyzer 51, such as a GC or density measurement device. Control of the concentration profile via analyzer 51 and as described above with respect to FIGS. 8-13 may then be used to enhance the performance of the column and conversion of dienes within reaction zone 46.

While described above with respect to selective hydrogenation of C5s, control of catalytic distillation reactor systems via controlling a density profile or a concentration profile of a selected non-key component may be extended to other mixed hydrocarbon feeds. For example, processing of close boiling C4 fractions, C6 fractions, C7 fractions, and the like in a catalytic distillation reactor system may benefit from density or concentration profile control, enhancing the performance of such catalytic distillation reactor systems with respect to reaction zone efficiency and product recovery efficiency. Such catalytic distillation reactor systems may be used for dimerization, oligomerization, hydrogenation, desulfurization, isomerization, etherification, dehydrogenation, back cracking, disproportionation, transesterification, or other various reactions known to benefit from LeChatalier's principle via concurrent reaction and separation.

EXAMPLE 4

Simulations were conducted to give an example of how to determine the appropriate sample locations of a catalytic distillation reactor system for selectively hydrogenating a C5 feed stream. The C5 feed composition is shown in Table 14. Simulations were carried out in ASPEN PLUS 7.3.2 (Aspen Technology, Inc., Burlington, Mass.). The reactions considered in the simulation are provided in Table 15. Simulations for columns were performed with the column configurations in Table 16. Two simulations were performed to check the effect of bottom flow rate on change of total inert and a summation of cyclopentene and cyclopentane along the column.

TABLE 14

| C5 Feed Composition to C5CDhydro column (wt. %) | |
| --- | --- |
| ISOBUTYLENE | 0.0022% |
| 1-BUTENE | 0.0005% |
| N-PENTANE | 5.3794% |
| 2-METHYL-BUTANE | 4.4459% |
| CYCLOPENTANE | 40.8229% |
| CYCLOPENTENE | 5.4332% |
| CYCLOPENTADIENE | 4.1475% |
| DICYCLOPENTADIENE | 0.1046% |
| 1-PENTENE | 5.1483% |
| CIS-2-PENTENE | 1.3293% |
| TRANS-2-PENTENE | 2.6058% |
| 2-METHYL-1-BUTENE | 2.1779% |
| 2-METHYL-2-BUTENE | 3.4958% |

TABLE 14-continued

C5 Feed Composition to C5CDhydro column (wt. %)

| | |
|---|---|
| 3-METHYL-1-BUTENE | 0.4424% |
| 2-METHYL-1,3-BUTADIENE | 9.8304% |
| CIS-1,3-PENTADIENE | 3.2129% |
| 1-TRANS-3-PENTADIENE | 6.7781% |
| 1,4-PENTADIENE | 2.7135% |
| 1,2-PENTADIENE | 0.0663% |
| N-HEXANE | 0.0691% |
| 2-METHYL-PENTANE | 0.0462% |
| 3-METHYL-PENTANE | 0.0537% |
| 2,2-DIMETHYL-BUTANE | 1.6329% |
| 2-ETHYL-1-BUTENE | 0.0011% |
| BENZENE | 0.0023% |
| Others | 0.0581% |

TABLE 15

Reactions considered in the Aspen Plus simulation

1-TRANS-3-PENTADIENE + HYDROGEN --> TRANS-2-PENTENE
CIS-1,3-PENTADIENE + HYDROGEN --> CIS-2-PENTENE
1,2-PENTADIENE + HYDROGEN --> TRANS-2-PENTENE
1,4-PENTADIENE + HYDROGEN --> TRANS-2-PENTENE
2-METHYL-1,3-BUTADIENE + HYDROGEN --> 2-METHYL-2-BUTENE
CYCLOPENTADIENE + HYDROGEN --> CYCLOPENTENE

TABLE 16

Simulation Conditions

| Case Number | 1 | 2 |
|---|---|---|
| Column Stages | 102 | 102 |
| C5 Feed Stage | 72 | 72 |
| Hydrogen Feed Stage | 95 | 95 |
| Reaction Zone Stages | 60-70 | 60-70 |
| | 73-82 | 73-82 |
| Pressure (psia) | 135 | 135 |
| Reflux Ratio | 7.5 | 7.5 |
| C5 Feed rate (lb/h) | 17999.0 | 17999.0 |
| H2 feed rate (lb/hr) | 300.53 | 300.53 |
| Bottoms rate (lb/hr) | 9358.3 | 9561.7 |

Figure 14:
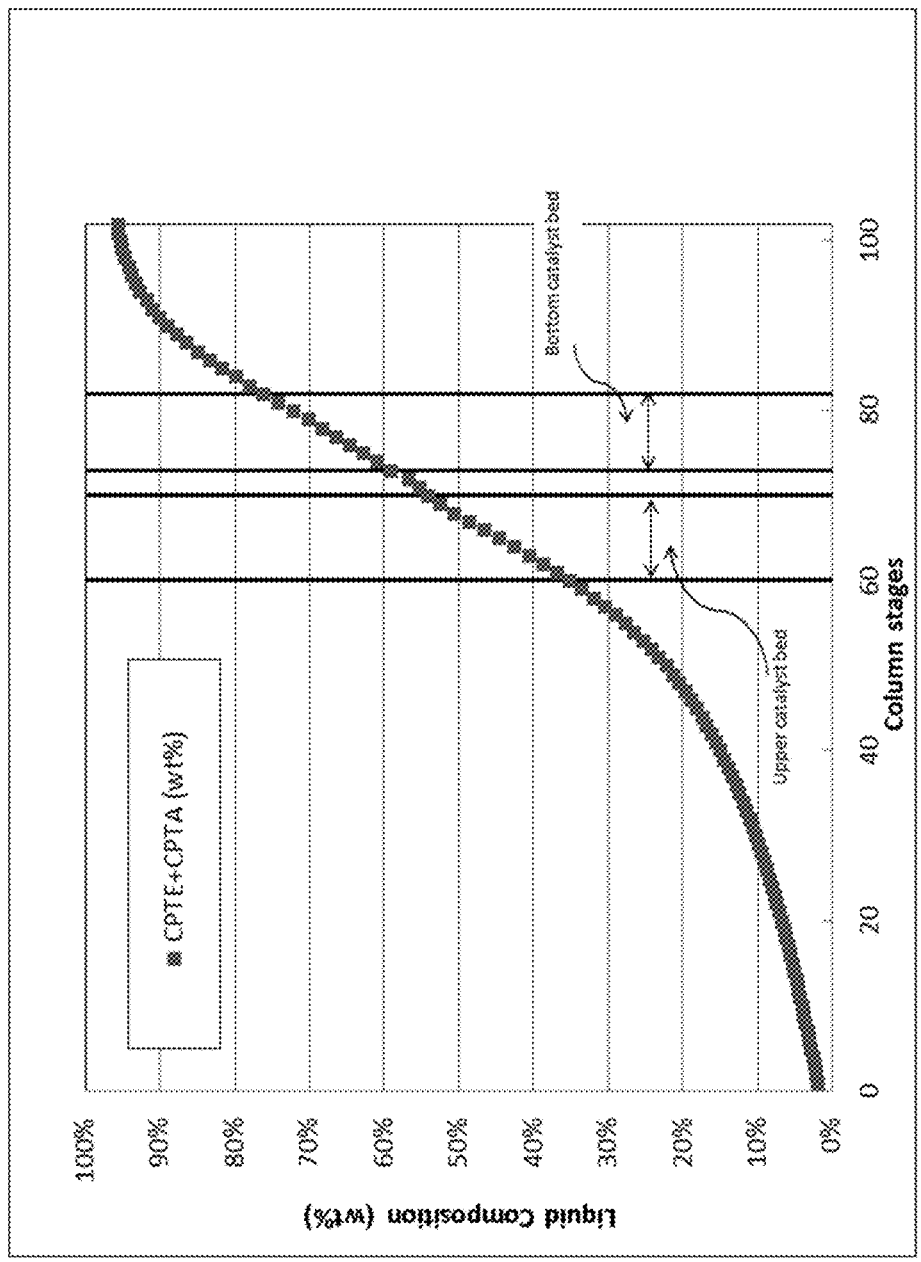
FIGS. 14-16 illustrate simulation results for processes according to embodiments disclosed herein.
Figure 15:
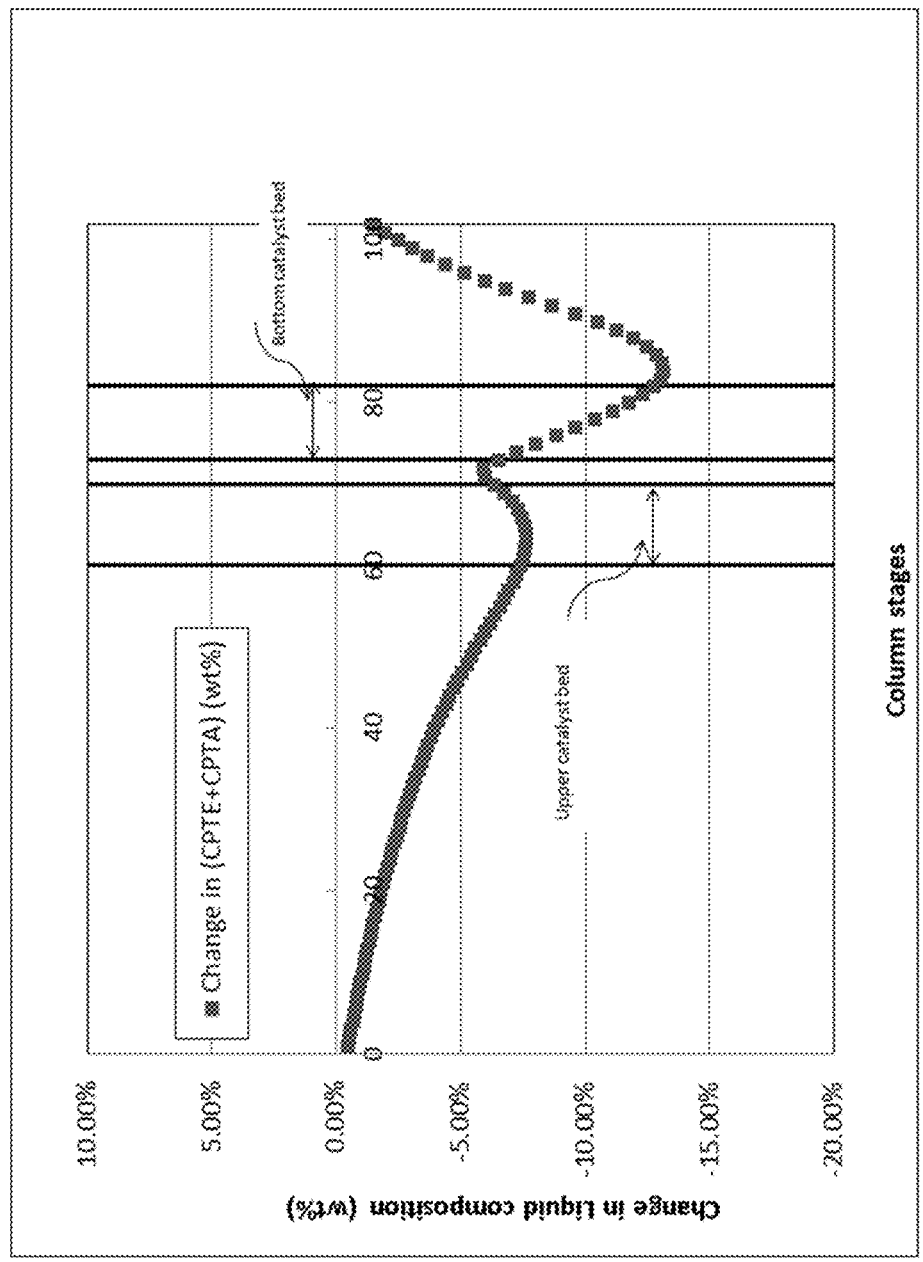

FIG. 14 illustrates the concentration profile for cyclopentene plus cyclopentane within the column for Simulation Condition 1. The concentration of cyclopentene and cyclopentane increases slowly moving from the top of the column (stage 1) downward, increases significantly within the catalyst beds, and then leveling off closer to the bottom between stages 90 and 102. FIG. 15 is a graph depicting the change in the concentration profile for cyclopentane plus cyclopentene after the column reaches equilibrium at the conditions for Simulation Condition 2.

It can be seen from FIGS. 14 and 15 that after increasing the bottoms draw rate from 9358.3 lb/h to 9561.7 lb/h, a noticeable change in the summation of cyclopentane and cyclopentene (above 5%) occurs from stage 46 to stage 96, and the change is at an approximate peak value at stage 85. This suggests that a good sample point may thus be located between stages 80 and 90, for example, for determining whether or not the concentration profile is moving up or down the column. However, this doesn't rule out additional sample points in column overhead stream, mid-reflux stream, and bottom stream because these three streams are typically easily accessible.

Figure 16:
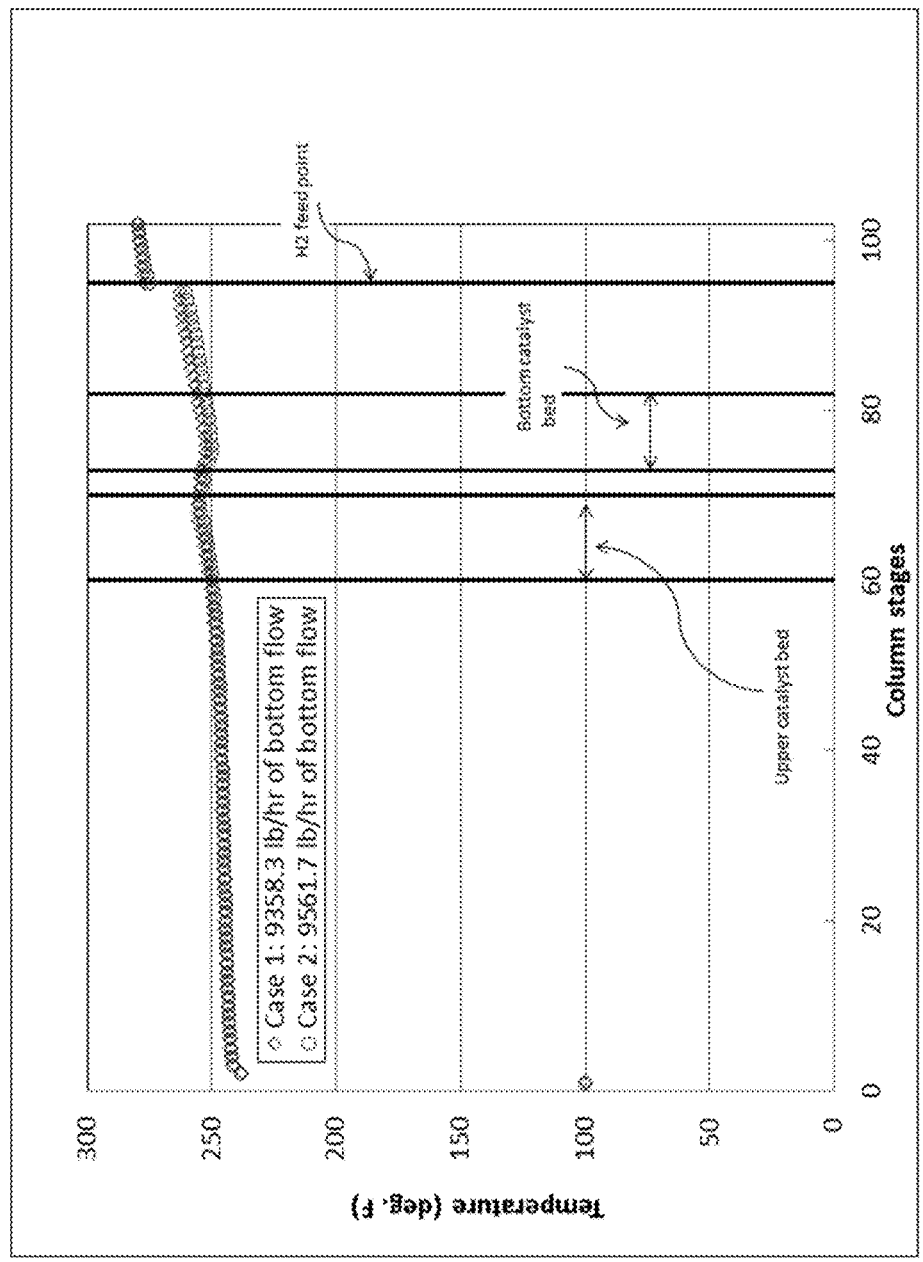

FIG. 16 illustrates the temperature profile within the column for Simulation Conditions 1 and 2. As can be seen, there are only minor changes in the column temperature profile after increasing column bottom flow rate from 9358.3 lb/h to 9561.7 lb/h. From this result, it can be appreciated that temperature control for C5CDHydro column may be difficult. As described below, pilot plant experiments confirmed this result.

EXAMPLE 5: EXPERIMENTAL EXAMPLE

Steam cracker C5 dienes selective hydrogenation over a palladium catalyst (about 0.6 wt % palladium on a support) and a nickel-based catalyst (about 33.3 wt % nickel oxide on a support) were studied in a pilot plant. The objective of the pilot plant experiments was to reduce dienes from very high levels down to a very low level while minimizing the loss of unsaturates. In particular linear olefin recovery was considered more important than iso-olefin recovery because, in a downstream of methathesis unit, one mole linear C5 olefin can theoretically produce three moles of propylene, while one mole of branched C5 olefin can produce one mole of propylene. Two pilot plant configurations were used, the first corresponding to FIG. 17 (feed purification) plus FIG. 18 (composition based control similar to the embodiment of FIG. 8), the second corresponding to FIG. 17 plus FIG. 19 (composition based control similar to the embodiment of FIG. 9)

Figure 17:
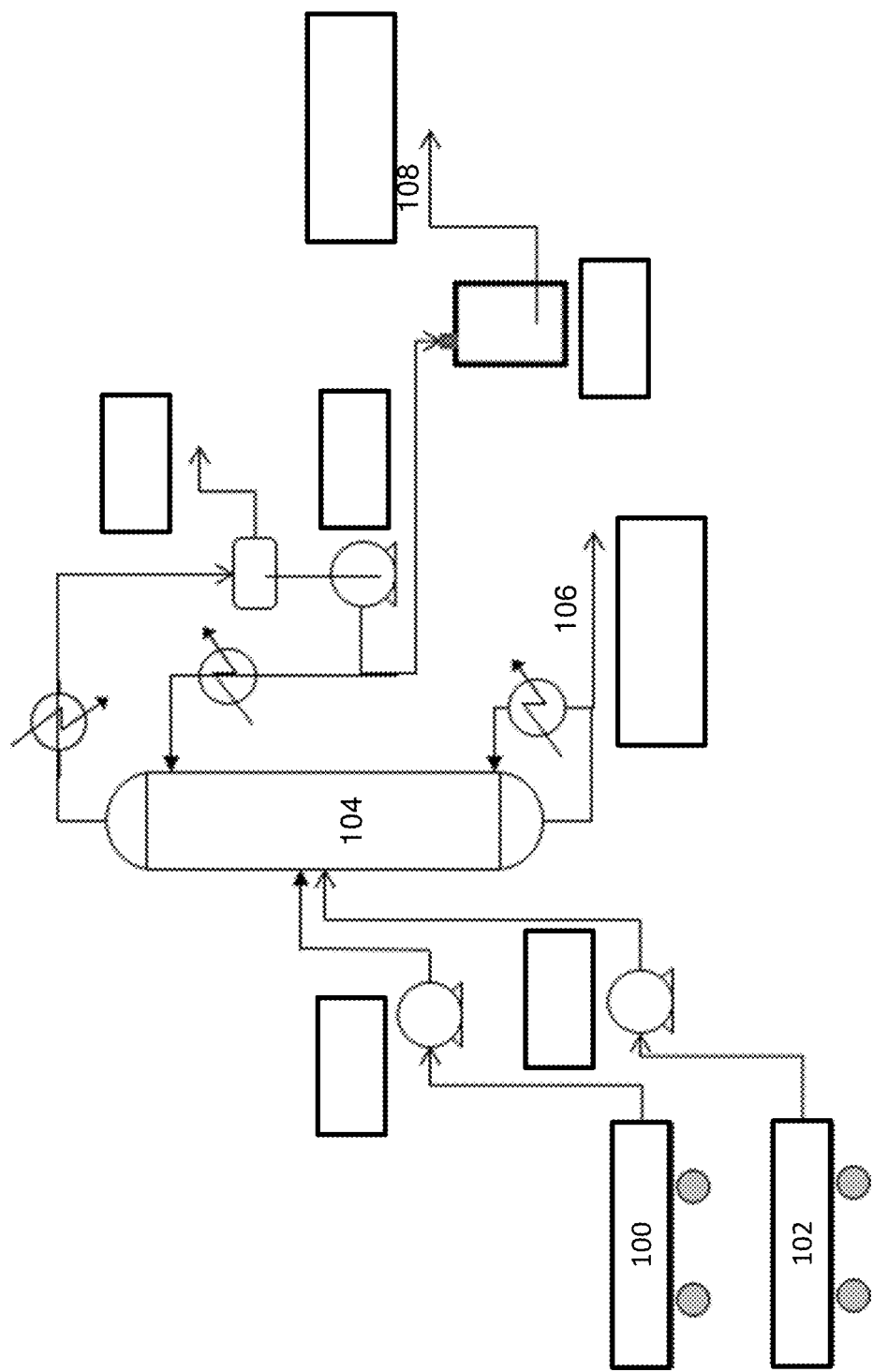
FIGS. 17-19 are simplified flow diagrams of pilot plant setups used to investigate processes to produce C5 olefins according to embodiments disclosed herein.

Referring now to FIG. 17, C5 feed purification was performed by feeding a pygas 100 and a cyclopentane stream 102 to a distillation column 104. Column 104 was entirely filled with Raschig super rings. The aromatics and C6+ hydrocarbons were separated as bottom product 106 while the C5 hydrocarbons were recovered in the overhead stream 108. The overhead product stream was then used as a feed to the catalytic distillation reactor systems described below with respect to FIGS. 18 and 19.

Figure 18:
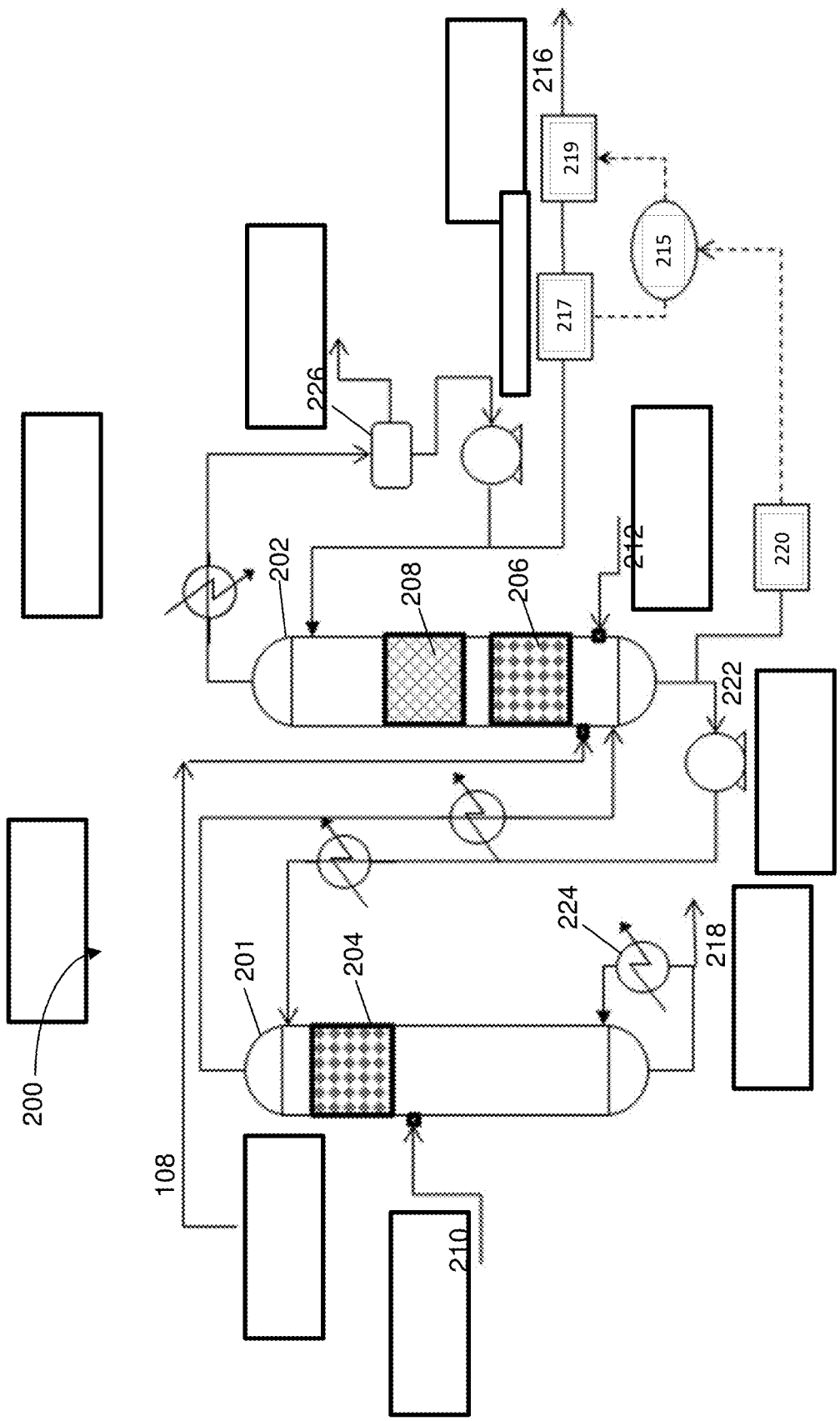
Figure 19:
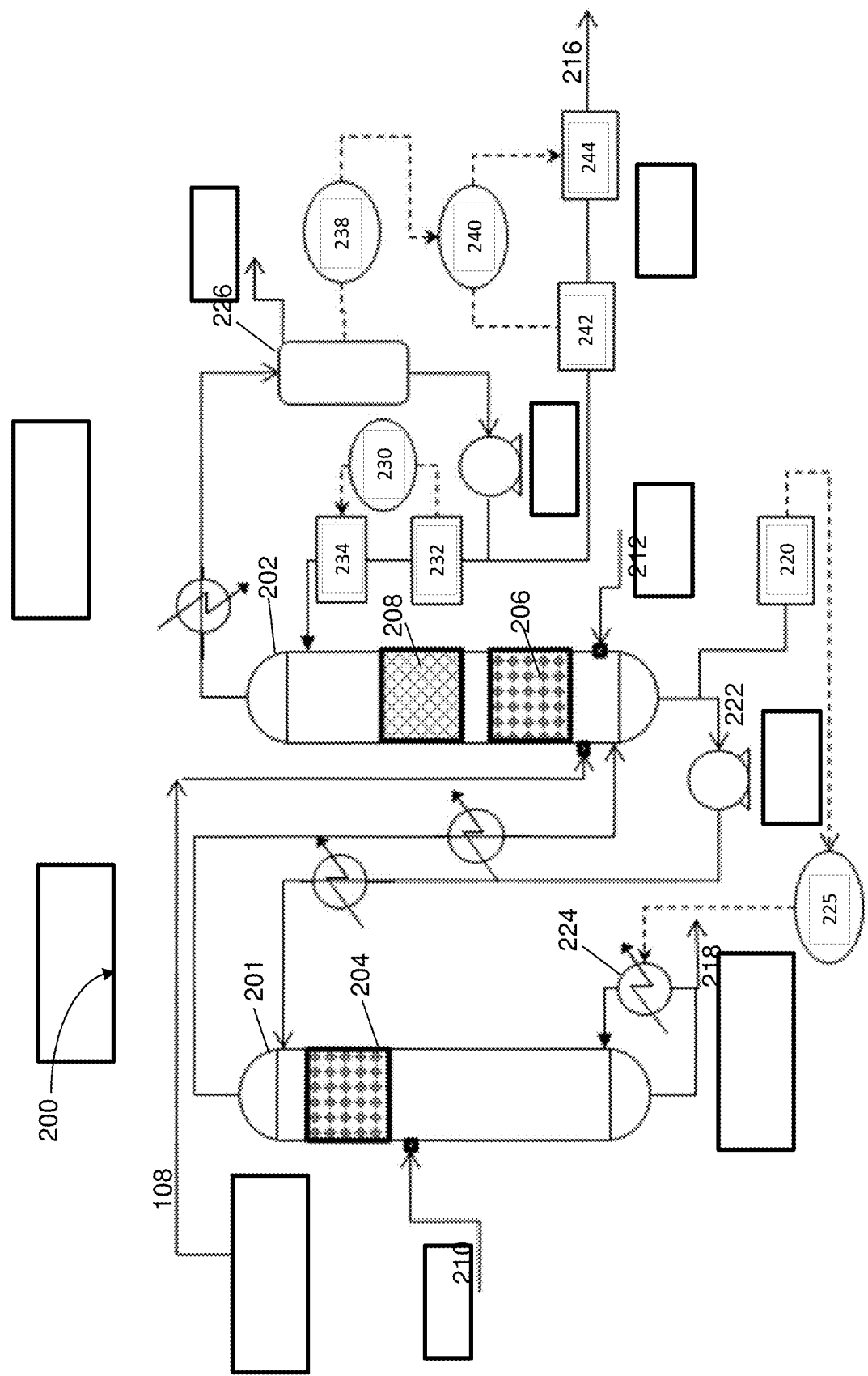

The catalytic distillation reactor systems 200 of FIGS. 18 and 19 are similar, column 200 being split into a stripping section 201 and a rectifying section 202. The stripping section 201 (below the elevation of feed 108 introduction) includes one reaction zone 204 containing a selective hydrogenation catalyst, and the rectifying section (above the elevation of feed 108 introduction) includes tow reaction zones 206, 208 containing a selective hydrogenation catalyst. Hydrogen 210, 212 is introduced below reaction zones 204, 206, respectively. Dienes in feed 108 are converted within column 200 to olefins and recovered in the distillate product 216. The catalyst zones 206, 208 above the feed were used to convert light dienes such as isoprene and cyclopentadiene. Heavier linear dienes traverse down and were reacted in catalyst zone 204 to prevent significant yield loss to the bottoms product 218. Rectifying section 202 was charged with 8 ft of Raschig super rings at the top followed by 14 ft of palladium catalyst and 7 ft of nickel catalyst. Stripper section 201 was filled with 6 ft of Raschig super rings at the top followed by 7 ft of nickel catalyst and 18 ft of Raschig super rings.

Referring now to FIG. 18, column 200 is configured for cyclopentane plus cyclopentene composition profile control, where an analyser 220 is disposed in the mid-reflux line 222. The control system is configured to control the composition profile via adjustment of the draw rate of overhead product stream 216 (i.e., column overhead flow control is used to optimize the cyclopentane and cyclopentene profile in the mid-reflux stream). Based on an output from analyser 220, the flow control loop 215 on the overhead draw, including flow meter 217 and control valve 219, is adjusted. When the summation of cyclopentane and cyclopentene increases and deviates from the set-point, the overhead flow is reduced while the reflux flow is increased (i.e., cascaded to overhead drum level). When the summation of cyclopentane and cyclopentane becomes less than the set point, the overhead flow is increased which at the same time the reflux flow is decreased (i.e., cascaded to overhead drum level).

Referring now to FIG. 19, column 200 is also configured for cyclopentane plus cyclopentene composition profile control, where an analyzer 220 is disposed in the mid-reflux line 222. The control system 225 is configured to control the composition profile via adjustment of the heat input to reboiler 224 (i.e., reboiler heat input is used to optimize the cyclopentane and cyclopentene profile in the mid-reflux stream). Column reflux flow is kept constant via flow control loop 230 (including flow meter 232 and control valve 234) and the overhead draw rate is allowed to vary based on level control in drum 226, where the level controller 238 is cascaded to flow control loop 240 (including flow meter 242 and control valve 244). For example, when the cyclopentane profile moves up and away from the set point, the reboiler duty is decreased and hence less liquid is accumulated in the overhead drum 226. The overhead flow is cascaded to the overhead drum level and thus the overhead flow is reduced while the reflux flow is maintained at the same rate.

Figure 20:
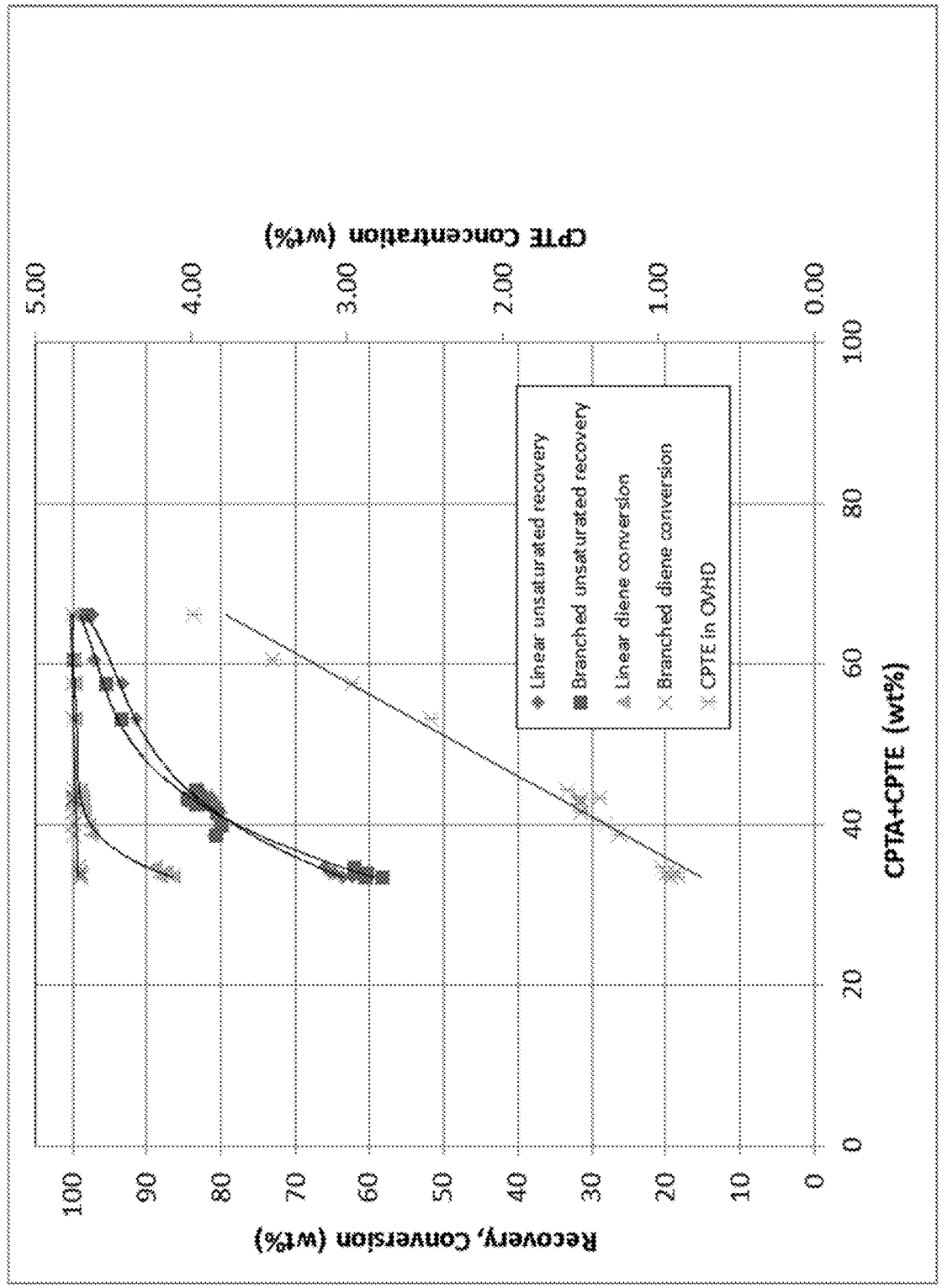
FIG. 20 is a chart illustrating pilot plant experimental results.

FIG. 20 provides a summary of the pilot plant data, including the measured linear/branched C5 olefin recovery rate, C5 diene conversion and cyclopentene concentration in the overhead stream plotted against the summation of cyclopentane and cyclopentene measured in the mid-reflux stream. It can be seen that below about 50 wt % of cyclopentane and cyclopentene concentration in the mid-reflux stream, either linear or branched C5 olefin recovery and diene conversion deteriorated significantly. Above around 50 wt % of cyclopentane and cyclopentene concentration in the mid reflux stream, either branched or linear C5 olefin recovery starts to level off. There is almost a linear relationship between the cyclopentene concentration in the overhead stream vs. the total cyclopentane and cyclopentene in the mid reflux stream.

The pilot plant runs illustrate that a composition profile control may be used to operate a column at close to 100% diene conversion (hence very little or no diene will be present in the C5 olefin product stream) while maximizing C5 olefin recovery rate (typically higher than ~90%) and at the same time controlling cyclopentene concentration in the overhead C5 olefin product. While the cyclopentene concentration in the overheads of the pilot plant system was a little higher than the desired 0.5 wt %, more distillation stages above the catalyst bed or an ensuing cyclopentene removal column may be used to reduce cyclopentene level.

As described above, various embodiments may include a heat soaker 32. In some embodiments, however, a heat soaker is not required, as will be described below. Typically, in prior art processes, the above noted problems associated with steam cracker C5 feeds or similar feedstocks containing relatively high amounts of highly reactive species are solved by use of a heat soaker, also known as a dimerization reactor, to dimerize the cyclopentadiene and form dicyclopentadiene. This reaction occurs before any initial separator or partial hydrogenation unit. Heat soakers, from an energy standpoint, are costly to operate and require the use of additional supporting equipment.

The effluent from the heat soaker, which will include linear and branched C5 olefins, linear and branched C5 dienes, dicyclopentadiene, cyclic C5 olefins, and other C6+ hydrocarbons, among others, is then typically fed to a convention distillation column operated in mixed liquid/vapor flow. In the distillation column, C6+ hydrocarbons, including dicyclopentadiene, are separated from the linear, branched, and cyclic C5 olefins. As noted, this method of cyclopentadiene removal is energy intensive and requires additional process equipment.

Alternatively, it has been found that the use of a distillation column operated in liquid continuous mode may advantageously replace the conventional distillation column operated in mixed liquid/vapor mode. Due to the liquid continuous mode, improved mixing, and improved heat profile, it has also been found that cyclopentadiene may undergo Diels Alder reaction in the distillation column to dimerize the cyclopentadiene and form dicyclopentadiene. As a result, the heat soaker may also be removed while retaining the dimerization function.

Accordingly, embodiments disclosed herein relate to an improved process for producing C5 olefins with limited cyclopentadiene and other dienes in the product stream without the need for expensive heat soakers or dimerization reactors. Eliminating a heat soaker and replacing the conventional distillation column with a liquid continuous distillation column may allow for the reduction in process equipment, lower operating cost, and simplicity of operation while retaining the dimerization function of the heat soaker.

Figure 21:
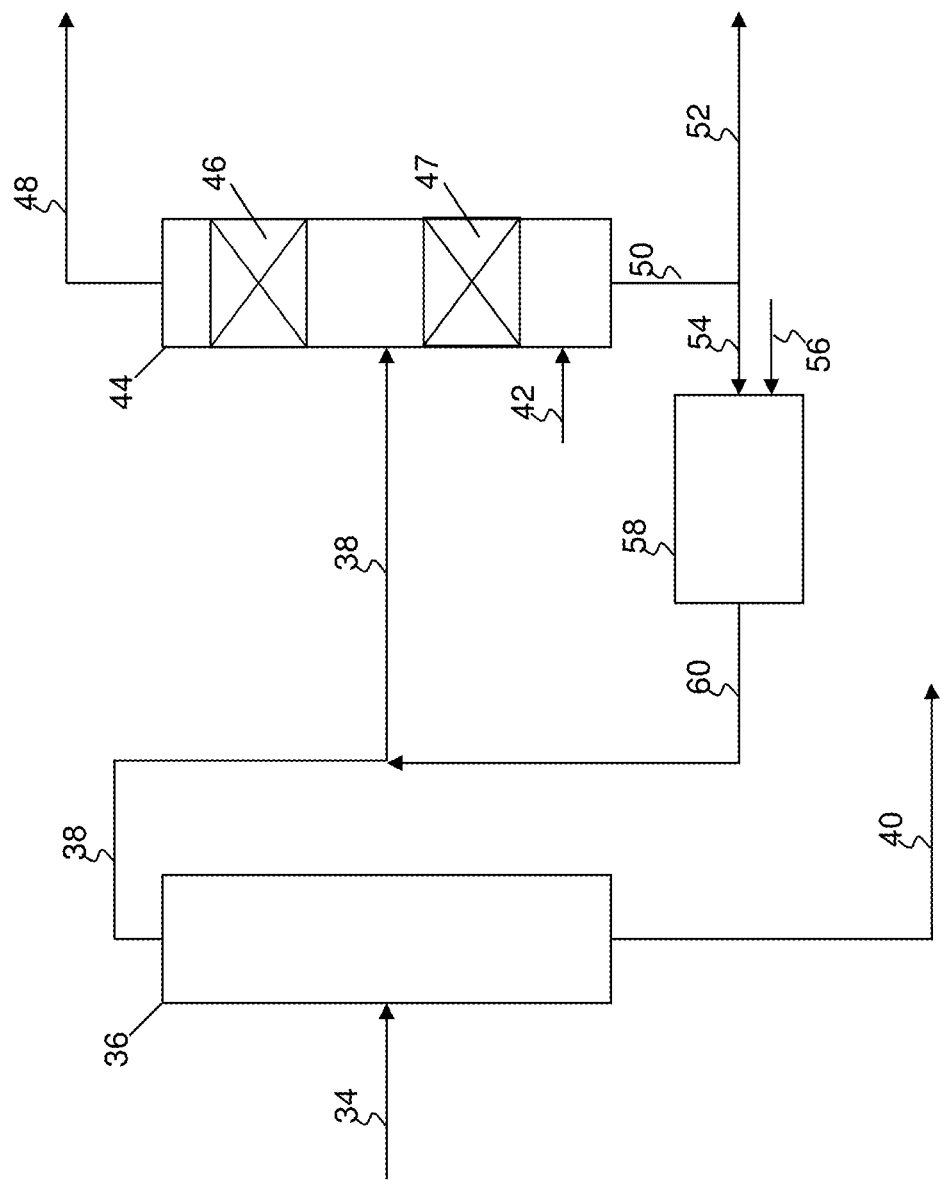
FIG. 21 is a simplified flow diagram of a process to produce C5 olefins according to embodiments disclosed herein.

FIG. 21 illustrates an improved process for producing C5 olefins from a mixed hydrocarbon stream utilizing a liquid continuous distillation column for the concurrent dimerization and removal of cyclopentadiene. According to embodiments disclosed herein, hydrocarbon stream 35, such as a steam cracker C5 feed, may contain cyclopentadiene, linear and branched C5 olefins, linear and branched C5 dienes, cyclic C5 olefins, and C6+ hydrocarbons, among other components as described above. Mixed hydrocarbon stream 34 may be fed to a low temperature/low pressure distillation column 36, such as a bubble type distillation column operating in liquid continuous mode. In the distillation column, cyclopentadiene is dimerized to form dicyclopentadiene. Additionally, cyclopentadiene may be reacted with other compounds, such as isoprene, to form heavy olefin compounds.

Concurrently, distillation column 36 may also fractionate the mixed stream to form a bottoms fraction 40 containing the C6+ hydrocarbons, dicyclopentadiene, and other heavy components, and an overheads fraction 38 containing the linear, branched, and cyclic C5 olefins, and the linear and branched C5 dienes. Any sulfur compounds contained in the mixed hydrocarbon stream may also be recovered with bottoms fraction 40. To obtain the desired separation, distillation column 36 may be controlled to limit the overhead fraction benzene content to less than 0.5 wt %, for example.

The overhead fraction 38 may then be recovered and fed to a catalytic distillation reactor system 44 and processed as described above.

The distillation column 36 may be a low temperature/low pressure separator, such as a distillation column operated in liquid continuous mode. The column may be operated at a pressure in the range from about 15 psia to about 85 psia, such as from about 20 psia to about 80 psia or from about 25 to about 75 psia, and at a condenser temperature in the range from about 90° F. to about 150° F., such as from about 110° F. to 145° F. or from about 120° F. to about 135° F. As noted above, distillation column 36 may be controlled, such as via reflux rate and distillate to feed ratio, to minimize the amount of sulfur containing compounds and benzene in lower boiling fraction 38, and to minimize the amount of valuable olefins and dienes (to be converted to olefins downstream) recovered with higher boiling fraction 40. The residence time in the liquid continuous distillation column should be sufficient to convert the cyclopentadiene to dicyclopentadiene, while limiting the thermal reaction of other components, as the dienes may be converted to desirable olefins in reactor system 44, as described above. The residence may in the range of about 0.2 hours to about 6 hours, such as in the range from about 1.5 hours to about 3 hours. In some embodiments, the dimerization reaction conditions of temperature, pressure, and residence time are controlled to achieve at least 90% conversion of the cyclopentadiene, such as at least 92%, at least 93%, at least 93% or at least 94% cyclopentadiene conversion to heavier compounds, such as dicyclopentadiene. Various manners of operating such a liquid continuous distillation column are described in U.S. Pat. No. 7,287,745, herein incorporated by reference. Advantageously, it has been found that a liquid continuous distillation column in C5 service may effectively operate as both a heat soaker and separator.

EXAMPLE 6

Simulations were conducted to compare the performance of systems for selectively hydrogenating a C5 feed stream according to various embodiments herein. Simulations were carried out in ASPEN PLUS 7.2 (Aspen Technology, Inc., Burlington, Mass.).

In this Example, a process similar to that as illustrated in FIG. 21 is simulated. In the simulations, dienes and acetylenes are assumed to be selectively hydrogenated into olefins in the catalytic distillation reactor system, and all olefins are assumed to be saturated into alkanes in the total hydrogenation unit. Process conditions were as follows.

TABLE 17

Process Conditions for Example 1

| Case# | 1 |
|---|---|
| Low P/T column | |
| Pressure, psia | 27 |
| Column stages | 30 |
| Condenser temp, ° F. | 130 |
| Reboiler temp, ° F. | 259 |
| Feed stage | 14 |
| Dimerization/Liquid continuous | 10-30 |
| Thiophene in distillate, ppm | 0 |
| Benzene in distillate, wt % | 0.5 wt % |
| C5 olefin recovery, % | 100% |
| C5CDHydro column | |
| Column stages | 102 |
| C5 feed stage | 42 |
| H2 feed stage | 60 |
| Hydrogenation reaction zone | 30-40 |
| | 43-50 |
| Cyclopentene in OVHD, wt % | 0.46% |
| Linear olefin recovery, % | 89.95% |
| Total olefin recovery, % | 89.44% |
| Pressure, psia | 135 |
| Mass reflux ratio | 10.68 |
| Bottom vs. feed molar ratio | 0.442 |
| PPH2, psi | 15.6 |
| Total Hydrogenation Unit | |
| Pressure, psia | 260 |
| Temperature, ° F. | 230 |
| PPH2, psi | 181 |
| Recycle vs. feed molar ratio | 0.81 |

The simulated mass balance for Example 6 is shown in Table 18.

TABLE 18

| Mass Flow lb/hr | Pygas Feed | Low PT Col OVHD | Low PT Col BTMS | Recycle Stream | HTU PRD | CDHydro OVHD | CDHydro purge | Vent Loss |
|---|---|---|---|---|---|---|---|---|
| C4s | 46.29 | 46.29 | 0.00 | 0.00 | 0.00 | 27.23 | 0.00 | 19.07 |
| N-PENTANE | 576.77 | 375.70 | 0.01 | 4.36 | 32.90 | 553.04 | 1.02 | 51.25 |
| 2-METHYL-BUTANE | 641.04 | 641.04 | 0.00 | 0.00 | 65.47 | 216.33 | 0.00 | 89.95 |
| CYCLOPENTANE | 89.64 | 83.90 | 5.79 | 2592.15 | 3116.81 | 0.55 | 808.08 | 0.03 |
| CYCLOPENTANE | 651.13 | 645.65 | 5.53 | 509.58 | 0.00 | 26.69 | 119.53 | 1.85 |
| CYCLOPENTADIENE | 6718.23 | 16.79 | 0.00 | 0.00 | 0.00 | 0.00 | 0.00 | 0.00 |
| DICYCLOPENTADIENE | 0.00 | 0.00 | 6701.44 | 21.94 | 21.94 | 0.00 | 5.15 | 0.00 |
| 1-PENTENE | 713.41 | 713.40 | 0.01 | 0.00 | 0.00 | 637.80 | 0.00 | 81.60 |
| CIS-2-PENTENE | 118.40 | 118.38 | 0.02 | 14.90 | 0.00 | 846.75 | 3.51 | 57.20 |
| TRANS-2-PENTENE | 199.38 | 133.35 | 0.03 | 12.78 | 0.00 | 1383.18 | 3.98 | 125.03 |
| 2-METHYL-2-BUTENE | 448.22 | 448.21 | 0.01 | 0.01 | 0.00 | 398.90 | 0.00 | 49.31 |
| 2-METHYL-2-BUTENE | 0.00 | 0.00 | 0.00 | 63.63 | 0.00 | 1675.57 | 14.95 | 122.38 |
| 3-METHYL-2-BUTENE | 60.89 | 60.88 | 0.00 | 0.00 | 0.00 | 50.13 | 0.00 | 10.78 |
| 2-METHYL-1,3-BUTADIENE | 1833.04 | 1833.69 | 0.35 | 0.00 | 0.00 | 0.00 | 0.00 | 0.00 |
| CIS-1,3-PENTADIENE | 591.99 | 586.88 | 5.31 | 0.00 | 0.00 | 0.00 | 0.00 | 0.00 |
| 2-TRANS-3-PENTADIENE | 546.42 | 935.52 | 4.80 | 0.00 | 0.00 | 0.00 | 0.00 | 0.00 |
| 1,4-PENTADIENE | 847.86 | 347.86 | 0.00 | 0.00 | 0.00 | 0.00 | 0.00 | 0.00 |
| 1,2-PENTADIENE | 9.02 | 8.91 | 0.11 | 0.00 | 0.00 | 0.00 | 0.00 | 0.00 |
| BENZENE | 19148.80 | 39.82 | 19108.97 | 32.33 | 0.00 | 0.00 | 7.58 | 0.00 |
| C6+ | 22864.32 | 684.39 | 22179.94 | 3111.04 | 3356.37 | 0.00 | 729.75 | 0.00 |
| HYDROGEN | 0.00 | 0.00 | 0.00 | 0.00 | 89.29 | 1.10 | 0.00 | 457.33 |
| Total flow | 55999.93 | 7987.73 | 48012.27 | 6362.78 | 6462.78 | 6021.48 | 1492.51 | 1073.80 |

As can be seen in Table 18, substantially all of the cyclopentadiene in the feed gas (6718.23 lb/hr) is dimerized to dicyclopentadiene and removed in the column bottoms (6701.44 lb/hr). Only a small portion of cyclopentadiene remains in the column overheads (16.79 lb/hr), equating to a 99.75% conversion. Additionally, substantially all of the linear and branched olefins are recovered from the column overheads.

Advantageously, embodiments herein provide an efficient and effective means for recovering C5 olefins from steam cracker C5 cuts. In some embodiments, a dual catalyst system, including a nickel-based catalyst and a palladium-based catalyst, has been found to be highly selective toward the desired olefin product, provide a high olefin recovery percentage, and to be very robust. In other aspects, it has been found that controlling a composition profile of an inert or diluent compound within a catalytic distillation reactor system may be used to optimize reaction within the catalyst beds as well as product recovery and purity.

Embodiments herein are described as useful for processing of stream cracker C5 feeds. Similar C5 cuts containing relatively high amounts of highly reactive species may also be processed according to embodiments herein. However, due to the relatively low level of highly reactive species typically found in an FCC cut, processes related to FCC feedstocks may not be viewed as relevant, as one skilled in the art would not look toward processing of such feeds in this manner due to the unnecessary additional capital and operating expenses that would be incurred.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A process for the selective hydrogenation of C5 dienes in a mixed C5 hydrocarbon stream, comprising:
feeding hydrogen and a C5-olefin containing stream comprising linear pentenes, dienes, acetylenes, and a diluent compound to a catalytic distillation reactor system;
concurrently in the catalytic distillation reactor system:
hydrogenating the acetylenes and dienes; and
fractionating the C5-olefin containing stream;
recovering an overheads fraction comprising the pentenes;
recovering a bottoms fraction;
wherein the catalytic distillation reactor system has at least three reaction zones, including:
a first reaction zone disposed below a C5-olefin containing stream feed elevation and containing a nickel-based hydrogenation catalyst;
a second reaction zone disposed above the C5-olefin containing stream feed elevation and containing a nickel-based hydrogenation catalyst; and
a third reaction zone disposed above the second reaction zone and containing a palladium-based hydrogenation catalyst;
purging a portion of the bottoms fraction;
reacting a remaining portion of the bottoms fraction in a total hydrogenation unit to convert cyclic C5 olefins to cyclopentane; and
recycling the cyclopentane to the catalytic distillation reactor system.

2. The process of claim 1, wherein the nickel-based catalyst comprises from about 5 wt % to about 30 wt % nickel, wherein the nickel-based hydrogenation catalyst is disposed on a diatomaceous earth support, has a BET surface area in the range from about 20 $m^2/g$ to about 400 $m^2/g$, and has a pore volume in the range from about 0.2 ml/g to about 0.7 ml/g, and wherein the palladium-based hydrogenation catalyst comprises from about 0.2 to about 1.0 wt % palladium disposed on an alumina support.

3. The process of claim 1, further comprising feeding the overheads fraction from the catalytic distillation reactor system to a metathesis unit and converting the linear C5 olefins to propylene.

4. The process of claim 1, further comprising separating the overheads fraction to recover a product fraction comprising linear C5 olefins and a recycle fraction comprising cyclopentene.

5. A process for the selective hydrogenation of C5 dienes in a mixed C5 hydrocarbon stream, comprising:
feeding hydrogen and a C5-olefin containing stream comprising linear pentenes, dienes, acetylenes, and a diluent compound to a catalytic distillation reactor system;
concurrently in the catalytic distillation reactor system:
hydrogenating the acetylenes and dienes; and
fractionating the C5-olefin containing stream;
recovering an overheads fraction comprising the pentenes;
recovering a bottoms fraction;
wherein the catalytic distillation reactor system has at least three reaction zones, including:
a first reaction zone disposed below a C5-olefin containing stream feed elevation and containing a nickel-based hydrogenation catalyst;
a second reaction zone disposed above the C5-olefin containing stream feed elevation and containing a nickel-based hydrogenation catalyst; and
a third reaction zone disposed above the second reaction zone and containing a palladium-based hydrogenation catalyst,
wherein the nickel-based catalyst comprises from about 5 wt % to about 30 wt % nickel, wherein the nickel-based hydrogenation catalyst is disposed on a diatomaceous earth support, has a BET surface area in the range from about 20 $m^2/g$ to about 400 $m^2/g$, and has a pore volume in the range from about 0.2 ml/g to about 0.7 ml/g, and wherein the palladium-based hydrogenation catalyst comprises from about 0.2 to about 1.0 wt % palladium disposed on an alumina support.

6. The process of claim 5, further comprising feeding the overheads fraction from the catalytic distillation reactor system to a metathesis unit and converting the linear C5 olefins to propylene.

7. The process of claim 5, further comprising separating the overheads fraction to recover a product fraction comprising linear C5 olefins and a recycle fraction comprising cyclopentene.

* * * * *